US012589132B2

(12) United States Patent
Barbee et al.

(10) Patent No.: US 12,589,132 B2
(45) Date of Patent: Mar. 31, 2026

(54) CD80 EXTRACELLULAR DOMAIN FC FUSION PROTEINS FOR TREATING PD-L1 NEGATIVE TUMORS

(71) Applicant: FIVE PRIME THERAPEUTICS, INC., Thousand Oaks, CA (US)

(72) Inventors: Susannah D. Barbee, San Francisco, CA (US); Thomas Brennan, Cupertino, CA (US); Barbara Sennino, San Francisco, CA (US)

(73) Assignee: FIVE PRIME THERAPEUTICS, INC., Thousand Oaks, CA (US)

( * ) Notice: Subject to any disclaimer, the term of this patent is extended or adjusted under 35 U.S.C. 154(b) by 761 days.

(21) Appl. No.: 17/432,640

(22) PCT Filed: Feb. 21, 2020

(86) PCT No.: PCT/US2020/019135
§ 371 (c)(1),
(2) Date: Aug. 20, 2021

(87) PCT Pub. No.: WO2020/172482
PCT Pub. Date: Aug. 27, 2020

(65) Prior Publication Data
US 2022/0031806 A1    Feb. 3, 2022

Related U.S. Application Data

(60) Provisional application No. 62/815,249, filed on Mar. 7, 2019, provisional application No. 62/809,319, filed on Feb. 22, 2019.

(51) Int. Cl.
*A61K 38/17*    (2006.01)
*A61P 35/00*    (2006.01)
*G01N 33/574*   (2006.01)

(52) U.S. Cl.
CPC .......... *A61K 38/1774* (2013.01); *A61P 35/00* (2018.01); *G01N 33/57492* (2013.01); *G01N 2333/70532* (2013.01)

(58) Field of Classification Search
CPC .. A61K 38/1774; A61K 38/177; A61K 38/00; A61P 35/00; G01N 33/57492; G01N 2333/70532; G01N 2800/52; C12Q 2600/106; C12Q 2600/158; C12Q 1/6886; C07K 14/70532; C07K 2319/30
See application file for complete search history.

(56) References Cited

U.S. PATENT DOCUMENTS

| | | | |
|---|---|---|---|
| 5,580,756 A | 12/1996 | Linsley et al. |
| 6,071,716 A | 6/2000 | Freeman et al. |
| 6,130,316 A | 10/2000 | Freeman et al. |
| 6,218,510 B1 | 4/2001 | Sharpe et al. |
| 6,294,660 B1 | 9/2001 | Sharpe et al. |
| 6,319,709 B1 | 11/2001 | Ostrand-Rosenberg et al. |
| 6,451,305 B1 | 9/2002 | Bosiotis et al. |
| 6,491,925 B2 | 12/2002 | Selvaraj et al. |
| 6,641,809 B1 | 11/2003 | Linsley et al. |
| 6,653,444 B1 | 11/2003 | Freeman et al. |
| 6,824,779 B1 | 11/2004 | Freeman et al. |
| 6,887,471 B1 | 5/2005 | Linsley et al. |
| 7,011,833 B1 | 3/2006 | Sturmhoefel et al. |
| 7,064,111 B1 | 6/2006 | Todo et al. |
| 7,070,776 B1 | 7/2006 | Linsley et al. |
| 7,183,376 B2 | 2/2007 | Punnonen et al. |
| 7,229,628 B1 | 6/2007 | Allison et al. |
| 7,311,910 B2 | 12/2007 | Linsley et al. |
| 7,619,078 B2 | 11/2009 | Sharpe et al. |
| 7,678,890 B2 | 3/2010 | Bosch |
| 7,749,718 B2 | 7/2010 | Chirica et al. |
| 7,968,680 B2 | 6/2011 | Green et al. |
| 8,114,845 B2 | 2/2012 | Langermann et al. |
| 8,268,788 B2 | 9/2012 | Epstein et al. |
| 8,956,619 B2 | 2/2015 | Ostrand-Rosenberg |
| 8,969,526 B2 | 3/2015 | Baehner et al. |
| 9,220,728 B2 | 12/2015 | Sadelain et al. |
| 9,308,236 B2 | 4/2016 | Miller et al. |
| 9,567,642 B2 | 2/2017 | Feldser et al. |
| 9,650,429 B2 | 5/2017 | Ostrand-Rosenberg et al. |
| 9,834,604 B2 | 12/2017 | Zhu et al. |
| 9,879,046 B2 | 1/2018 | Miller et al. |
| 10,273,281 B2 | 4/2019 | Brennan et al. |
| 2004/0236091 A1 | 11/2004 | Chicz et al. |
| 2009/0041790 A1 | 2/2009 | Rnak et al. |
| 2011/0044953 A1 | 2/2011 | Allison et al. |

(Continued)

FOREIGN PATENT DOCUMENTS

| | | |
|---|---|---|
| EP | 2 662 383 A1 | 11/2013 |
| EP | 2 856 876 B1 | 1/2018 |

(Continued)

OTHER PUBLICATIONS

Ribas et al., What does PD-L1 positive or negative mean? (J. Exp. Med. 2016 vol. 213 No. 13 2835-2840).*
Roach et al., Appl. Immunohistochem. Mol. Morphol. Development of a Companion Diagnostic PD-L1 Immunohistochemistry Assay for Pembrolizumab Therapy in Non-Small-cell Lung Cancer. July 24(6):392-397, 2016.*
PCT/US2020/19135 Search Report, Aug. 19, 2020.
Zhang L. et al., "Programmed cell death ligand 1 (PD-L1) expression on gastric cancer and its relationship with clinicopathologic factors", Int J Clin Exp Pathol, vol. 8, No. 9, p. 11084-11091, 2015.

(Continued)

*Primary Examiner* — Alana Harris Dent
(74) *Attorney, Agent, or Firm* — Melissa E. Karabinis

(57) ABSTRACT

The present disclosure provides methods of treating PD-L1 negative tumors, the methods comprising administering fusion proteins comprising the extracellular domain of human cluster of differentiation 80 (CD80) and the fragment crystallizable (Fc) domain of human immunoglobulin G 1 (IgG1).

22 Claims, 9 Drawing Sheets
Specification includes a Sequence Listing.

(56) References Cited

U.S. PATENT DOCUMENTS

| | | | |
|---|---|---|---|
| 2011/0059078 A1 | 3/2011 | Coyle et al. | |
| 2011/0223188 A1 | 9/2011 | Langermann | |
| 2013/0017199 A1 | 1/2013 | Langermann | |
| 2013/0149305 A1 | 6/2013 | Ostrand-Rosenberg et al. | |
| 2014/0377253 A1 | 12/2014 | Harding et al. | |
| 2016/0009805 A1* | 1/2016 | Kowanetz ........ | C07K 14/70532 |
| | | | 530/391.1 |
| 2016/0024179 A1 | 1/2016 | Warner et al. | |
| 2016/0251437 A1 | 9/2016 | Dong et al. | |
| 2017/0044268 A1 | 2/2017 | Gurney et al. | |
| 2017/0145071 A1 | 5/2017 | Brennan et al. | |
| 2017/0226181 A1 | 8/2017 | Ostrand-Rosenberg et al. | |
| 2017/0274073 A1 | 9/2017 | Grogan et al. | |
| 2017/0320959 A1 | 11/2017 | Swanson et al. | |
| 2018/0044400 A1 | 2/2018 | Kaempfer et al. | |
| 2018/0117145 A1 | 5/2018 | Selvaraj et al. | |
| 2018/0244749 A1 | 8/2018 | Swanson et al. | |
| 2019/0194288 A1 | 6/2019 | Brennan et al. | |

FOREIGN PATENT DOCUMENTS

| | | | |
|---|---|---|---|
| EP | 3 330 290 A1 | 6/2018 | |
| EP | 3 348 571 A1 | 7/2018 | |
| JP | 2011514150 A | 5/2011 | |
| WO | 1997/47732 A2 | 12/1997 | |
| WO | 1998/058965 A1 | 12/1998 | |
| WO | 2003/039486 A2 | 5/2003 | |
| WO | 2004/029197 A2 | 4/2004 | |
| WO | 2008/037080 A1 | 4/2008 | |
| WO | 2008/119071 A1 | 10/2008 | |
| WO | 2008/121821 A1 | 10/2008 | |
| WO | 2009/089149 A1 | 7/2009 | |
| WO | 2013/019906 A1 | 2/2013 | |
| WO | 2014/151006 A2 | 9/2014 | |
| WO | 2015/200119 A1 | 12/2015 | |
| WO | 2016007235 | 1/2016 | |
| WO | 2016/161239 A1 | 10/2016 | |
| WO | 2016/168771 A2 | 10/2016 | |
| WO | 2016/174200 A1 | 11/2016 | |
| WO | 2017/019846 A1 | 2/2017 | |
| WO | 2017/042816 A1 | 3/2017 | |
| WO | 2017/048878 A1 | 3/2017 | |
| WO | 2017079117 | 5/2017 | |
| WO | 2017/103291 A1 | 6/2017 | |
| WO | 2017/144681 A1 | 8/2017 | |
| WO | 2017/149150 A1 | 9/2017 | |
| WO | 2017/151818 A2 | 9/2017 | |
| WO | 2017/181152 A2 | 10/2017 | |
| WO | 2017/201210 A1 | 11/2017 | |
| WO | 2017/201352 A1 | 11/2017 | |
| WO | 2018/064190 A1 | 4/2018 | |
| WO | 2018/075978 A1 | 4/2018 | |
| WO | 2018/201014 A1 | 11/2018 | |
| WO | 2020/047087 A1 | 3/2020 | |
| WO | 2020/172482 A1 | 8/2020 | |
| WO | 2020/227062 A1 | 11/2020 | |

OTHER PUBLICATIONS

Paz-Ares et al, "CheckMate 227: A randomized, open-label phase 3 trial of nivolumab, nivolumab plus ipilimumab, or nivolumab plus chemotherapy versus chemotherapy in chemotherapy-naive patients with advanced non-small cell lung cancer (NSCLC)", Annals of Oncology, vol. 28, No. Suppl 2, Apr. 2, 2017 (Apr. 2, 2017), p. ii50-ii51.

Hunter et al, "PD-L1 Testing in Guiding Patient Selection for PD-1/PD-L1 Inhibitor Therapy in Lung Cancer", Molecular Diagnosis and Therapy,vol. 22, No. 1, p. 1-10, Nov. 8, 2017.

Guan et al, "Programmed Death Ligand-1 (PD-L1) Expression in the Programmed Death Receptor-1 (PD-1)/PD-L1 Blockade: A Key Player Against Various Cancers", Archives of Pathology & Laboratory Medicine, vol. 141, No. 6, p. 851-861, Jun. 1, 2017.

Brüggemann C et al, "Predictive value of PD-L1 based on mRNA level in the treatment of stage IV melanoma with ipilimumab", vol. 143, No. 10, p. 1977-1984, Jun. 14, 2017.

Horn et al, "Soluble CD80 Protein Delays Tumor Growth and Promotes Tumor-Infiltrating Lymphocytes", Cancer Immunology Research, vol. 6, No. 1, p. 59-68, Jan. 1, 2018.

Haile et al, "A Soluble Form of CD80 Enhances Antitumor Immunity by Neutralizing Programmed Death Ligand-1 and Simultaneously Providing Costimulation", Cancer Immunology Research, vol. 2, No. 7, p. 610-615, Apr. 2, 2014.

Swanson, Ryan, et al., CD80 vIgD-Fc proteins combine checkpoint antagonism and costimulatory signaling for potent antitumor immunity [Abstract], American Association for Cancer Research Annual Meeting 2018. https://aacrjournals.org/cancerres/article/78/13_Supplement/4550/628749/Abstract-4550-CD80-vIgD-Fc-proteins-combine.

Li et al., JBC 292:6799-6809 (2017).

Alegre, M-L., et al., "T-cell regulation by CD28 and CTLA-4," Nature Reviews Immunology 1:220-228, Macmillan Magazines Ltd., England (2001).

"Body Weight Information for C57BL/6J (000664)," Jackson Laboratory (JAX), available at http://www.jax.org/jax-mice-and-srvices/strain-datasheet-pages/body-eight-chart-000664 (Aug. 6, 2017), 2 pages.

Bhatia, S., et al., "Dynamic Equilibrium of B7-1 Dimers and Monomers Differentially Affects Immunological Synapse Formation and T Cell Activation in Response to TCR/CD28 Stimulation," The Journal of Immunology 184(4):1821-1828, The American Association of Immunologists, Inc., United States (2010).

Collins, M., et al., "The B7 family of immune-regulatory ligands," Genome Biology 6(6):223, BioMed Central Ltd., England, 7 pages (2005).

Contardi, E., et al., "CTLA-4 is constitutively expressed on tumor cells and can trigger apoptosis upon ligand interaction," Int. J. Cancer 117:538-550, Wiley-Liss, Inc., United States (2005).

Czajkowsky, D. M. et al."Fc-fion proteins: new developments and future perspectives," EMBO Molecular Medicine, 4(10): 1015-1028, Wiley Online Library, United States (2012).

Dalal, S.P., et al., "Mutated CD80 may facilitate T-cell activation by inhibiting PDL1-PD1 suppression and by costimulating," Cancer Res 73(8 Suppl): Abstract 1264, in Proceedings of the 104th Annual Meeting of the American Association for Cancer Research, Apr. 6-10, American Association for Cancer Research, United States (2013).

Del Val, I., et al., "Towards the implementation of quality by design to the production of therapeutic monoclonal antibodies with desired glycosylation patterns," Biotechnology Progress 26(6):1505-1527, American Institute of Chemical Engineers, United States (Dec. 2010).

Eastwood, D., et al., "Monoclonal antibody TGN1412 trial failure explained by species differences in CD28 expression on CD4+ effector memory T-cells," British Journal of Pharmacology 161:512-526, The British Pharmacological Society, England (2010).

Felix, J., et al., "Ipilimumab reshapes T cell memory subsets in melanoma patients with clinical response," Oncoimmunology 5(7):e1136045, Taylor & Francis Group, England, 10 pages (Feb. 18, 2016).

Findlay, L., et al., "Improved in vitro methods to predict the in vivo toxicity in man of therapeutic monoclonal antibodies including TGN1412," Journal of Immunological Methods 352(1-2):1-12, Elsevier B.V., Netherlands (2010).

Freeman, G.J., et al., "B7, a new member of the Ig superfamily with unique expression on activated and neoplastic B cells," J. Immunol. 143:2714-22, American Association of Immunologists, United States (1989).

Girard, T., et al., "CD80 and CD86 IgC domains are important for quaternary structure, receptor binding and co-signaling function," Immunology Letters 161:65-75, Elsevier B.V., Netherlands (2014).

Gogishvili, T., et al., "Rapid Regulatory T-Cell Response Prevents Cytokine Storm in CD28 Superagonist Treated Mice," PLoS One 4(2) :e4643, Public Library of Science, United States, 9 pages (2009).

(56) References Cited

OTHER PUBLICATIONS

Greaves, P. and Gribben, J.G., "The role of B7 family molecules in hematologic malignancy," Blood 121(5):734-744, American Society of Hematology, United States (2013).

Hünig, T., "The storm has cleared: lessons from the CD28 superagonist TGN1412 trial," Nature Reviews Immunology 12:317-318, Macmillan Publishers Limited, England (2012).

International Preliminary Report on Patentability for Application No. PCT/2016/059838, International Bureau of WIPO, Switzerland, mailed on May 8, 2018, 11 pages.

International Preliminary Report on Patentability International Application No. PCT/2018/029897, International Bureau of WIPO, Switzerland, mailed on Oct. 29, 2019, 7 pages.

International Search Report and Written Opinion for International Application No. PCT/2019/048560, European Patent Office, Netherlands, mailed Dec. 20, 2019, 21 pages.

International Search Report and Written opinion for International Application No. PCT/2020/028715, International Search Authority, United States, mailed Jul. 17, 2020, 13 pages.

International Search Report and Written Opinion for International Application No. PCT/2020/030946, European Patent Office, Netherlands, mailed Sep. 1, 2020, 21 pages.

Jones, S., et al., "Lentiviral Vector Design for Optimal T Cell Receptor Gene Expression in the Transduction of Peripheral Blood Lymphocytes and Tumor-Infiltrating Lymphocytes," Human Gene Therapy 20(6):630-640, Mary Ann Liebert, United States (2009).

Kakoulidou, M., et al., "Human Soluble CD80 is Generated by Alternative Splicing, and Recombinant Soluble CD80 Binds to CD28 and CD152 Influencing T-cell Activation," Scandinavian Journal of Immunology 66:529-537, Blackwell Publishing Ltd., England (2007).

Kaneko, Y., et al., "Anti-Inflammatory Activity of Immunoglobulin G Result from Fc Sialylation," Science 313:670-673, American Association for the Advancement of Science, United States (2006).

Klebanoff, C.A., et al., "Central memory self/tumor-reactive CD8+ T cells confer superior antitumor immunity compared with effector memory T cells," Proc Natl Acad Sci A 102(27):9571-9576, National Academy of Sciences, United States (2005).

Lechner, M.G., et al., "Chemokines, costimulatory molecules and fion proteins for the immunotherapy of solid tumors," Immunotherapy 3(11):1317-1340, Future Medicine, England (2011).

Lechner, M.G., et al., "Immunogenicity of murine solid tumor models as a defining feature of in vivo behavior and response to immunotherapy," J. Immunother. 36(9):477-489, Wolters Kluwer, United States (2013).

Linsley, P.S., et al., "Binding of the B Cell Activation Antigen B7 to CD28 Costimulates T Cell Proliferation and Interleukin 2 mRNA Accumulation," J. Exp. Med. 173:721-730, Rockefeller University Press, United States (Mar. 1991).

Linsley, et al., Human B7-1 (CD80) and B7-2 (CD86) Bind with Similar Avidities but Distinct Kinetics to CD28 and CTLA-4 Receptors, Immunity, vol. 1, 793-801, (1994).

Liu, A., et al., "Combination B7-Fc Fion Protein Treatment and Treg Cell Depletion Therapy," Clinical Cancer Research 11(23):8492-8502, American Association for Cancer Research, United States (2005).

Liu, L., "Antibody Glycosylation and Its Impact on the Pharmacokinetics and Pharmacodynamics of Monoclonal Antibodies and Fc-Fion Proteins," Journal of Pharmaceutical Sciences 104: 1866-1884, Elsevier, Netherlands (Apr. 2015).

Mahnke, Y.D., et al., "The who's who of T-cell differentiation: Human memory Tcell subsets," Eur J Immunol. 43(11):2797-2809, Wiley-VCH Verlag GmbH & Co. KGaA, Germany (2013).

Millward, M., et al., "FPT155001: A phase Ia/Ib study of FPT155 (CD80FC) in patients with advanced solid tumor," Journal of Clinical Oncology, 37(8): 2019 ASCOSITC Clinical Immuo-Oncology Symposium, (2019), 3 pages.

Oganesyan, V., et al., "Structural characterization of a human Fc fragment engineered for lack of effector functions," Acta Cryst. D64:700-04, International Union of Crystallography, Singapore (2008).

Ostrand-Rosenberg, S. et al., "Novel strategies for inhibiting PD-1 pathwaymediated immune suppression while simultaneoly delivering activating signals to tumor-reactive T cells," Cancer Immunology, Immunotherapy, 64(10): 1287-1293, Springer Link, Germany (2015).

Ostrand-Rosenberg, S., et al., "The programmed death-1 immune-suppressive pathway: barrier to antitumor immunity," The Journal of Immunology 193(8):3835-3841, The American Association of Immunologists, Inc., United States (2014).

Park, H-M., et al., "CD4 T-cells transduced with CD80 and 4-1BBL mRNA induce long-term CD8 T-cell responses resulting in potent antitumor effects," Vaccine 32:6919-6926, Elsevier Ltd., England (2014).

Peach, R.J., et al., "Both extracellular immunoglobin-like domains of CD80 contain residues critical for binding T cell surface receptors CTLA-4 and CD28," The Journal of Biological Chemistry 270(36):21181-21187, The American Society for Biochemistry and Molecular Biology, Inc., United States (1995).

Pützer, B.M., et al., "Interleukin 12 and B7-1 costimulatory molecule expressed by an adenovir vector act synergistically to facilitate tumor regression," Proc. Natl. Acad. Sci. A 94:10889-10894, The National Academy of Sciences, United States (1997).

R&D Systems, "Recombinant Human B7-1/CD80 Fc Chimera," Catalog No. 10107-B1, Revised Apr. 10, 2019, 2 pages.

Rajpal, A., et al., "Introduction: Antibody Structure and Function," Therapeutic FcFion Proteins 1(1):1-43, Wiley-VCH Verlag GmbH, Germany (2014).

Runyon, K., et al., "The combination of chemotherapy and systemic immunotherapy with soluble B7-immunoglobulin G leads to cure of murine leukemia and lymphoma and demonstration of tumor-specific memory responses," Blood 97:2420-2426, The American Society of Hematology, United States (2001).

Sallto, F., "Central memory and Effector Memory T Cell Subsets; Function, Generation, and Maintenance," Annual Review of Immunology, 22(1): 745-763, Annual Reviews, United States (2004).

Sansom, D.M., "CD28, CTLA-4 and their ligands: who does what and to whom?" Immunology 101:169-177, Blackwell Science Ltd., England (2000).

Sola, Ricardo J., "Giycosylation of Therapeutics Proteins: An Effective Strategy to Optimize Efficacy," Biodrugs, 24(1): 9-21, Springer, United States (2010).

Sturmhoefel, K., et al., "Potent Activity of Soluble B7-IgG Fion Proteins in Therapy of Established Tumors and as Vaccine Adjuvant," Cancer Research 59:4964-4972, American Association for Cancer Research, United States (1999).

Vessillier, S., et al., "Cytokine release assays for the prediction of therapeutic mAb safety in first-in man trials—Whole blood cytokine release assays are poorly predictive for TGN1412 cytokine storm," Journal of Immunological Methods 424:43-52, Elsevier B.V., Netherlands (May 7, 2015).

Waight, J.D., et al., "Selective Fc [gamma] R Co-engagement on APCs Modulates the Activity of Therapeutic Antibodies Targeting T cell Antigens," Cancer Cell 33(6):1033-1047, Cell Press, Netherlands (Jun. 2018).

Walker, L.S.K. and Sansom, D.M., "The emerging role of CTLA4 as a cellextrinsic regulator of T cell responses," Nature Reviews Immunology 11:852-863, Macmillan Publishers Limited, England (2011).

Weber, J.S., et al., "Ipilimumab increases activated T cells and enhances humoral immunity in patients with advanced melanoma," J Immunother. 35(1):89-97 (2012).

Yamaguchi, N., et al., "Induction of Tumor Regression by Administration of B7-Ig Fion Proteins: Mediation by Type 2 CD8+ T Cells and Dependence on IL-4 Production," The Journal of Immunology 172:1347-1354, The American Association of Immunologists, Inc., United States (2004).

(56) References Cited

OTHER PUBLICATIONS

Yao, S., et al., "Advances in targeting cell surface signaling molecules for immune modulation," Nature Reviews Drug Discovery 12:130-146, Macmillan Publishers Limited, England (2013).

* cited by examiner

Figure 3A

CD80 EXTRACELLULAR DOMAIN FC FUSION PROTEINS FOR TREATING PD-L1 NEGATIVE TUMORS

CROSS-REFERENCE TO RELATED APPLICATIONS

This application is a 35 U.S.C. § 371 National Phase Application of International Application No. PCT/US2020/019135, filed Feb. 21, 2020, which claims the benefit of U.S. Provisional Application No. 62/809,319, filed Feb. 22, 2019, and U.S. Provisional Application No. 62/815,249, filed Mar. 7, 2019, the content each of which is incorporated herein by reference in its entirety.

REFERENCE TO A SEQUENCE LISTING SUBMITTED ELECTRONICALLY VIA EFS-WEB

The content of th electronically submitted sequence listing (Name: 3986-0190002_SequenceListing_ST25.txt; Size: 16,590 bytes; and Date of Creation: Jul. 27, 2021) is herein incorporated by reference in its entirety.

FIELD

This application demonstrates that fusion proteins comprising an CD80 (B7-1) extracellular domain (ECD) and an immunoglobulin fragment crystallizable (Fc) domain are effective in treating tumors, regardless of the PD-L1 status. Accordingly, such fusion proteins can be used advantageously to treat PD-L1 negative tumors.

BACKGROUND

PD-1 (programmed cell death protein 1) is an immunologic checkpoint that is expressed on activated T cells. The PD-1 pathway is important in the tumor microenvironment, where PD-L1 (programmed cell death protein 1 ligand) expressed by tumors interacts with PD-1 to suppress T cell effector functions, thereby surpassing immune surveillance and tumor cell killing. In addition to tumor cells, PD-L1 can also be expressed by antigen presenting cells in the tumor microenvironment. Both PD-1 and PD-L1 antagonists have been approved for the treatment of cancers.

PD-L1 has been reported to bind CD80 (B7-1) and induce bidirectional inhibitory signaling in the absence of CD28 and CTLA-4 receptors for CD80 (Li et al., *JBC* 292:6799-6809 (2017).) Therefore, it has been proposed that CD80 proteins could act therapeutically by antagonizing the inhibitory PD-L1/PD-1 pathway to drive potent anti-tumor immunity (Swanson et al., *Cancer Research* 78: Abstract 4550 (2018).) Indeed, CD80 extracellular domain (ECD)-Fc fusion proteins have been shown to elicit potent antitumor activity.

However, PD-L1 is not expressed on all tumors. As a result, PD-L1 testing is required for the treatment of certain indications with inhibitors of PD-1 or PD-L1, such that tumors that do not express PD-L1 may not be eligible for the treatment. Accordingly, methods of treatment for PD-L1 negative tumors are needed.

SUMMARY

As demonstrated herein, the anti-tumor effect elicited by fusion proteins comprising the extracellular domain (ECD) of human cluster of differentiation 80 (CD80) and the fragment crystallizable (Fc) domain of human immunoglobulin G 1 (IgG1) is mediated via CD28 and CTLA-4, but not via PD-L1. Therefore, these fusion proteins are surprisingly able to treat tumors, regardless of their PD-L1 status. Accordingly, provided herein are methods of treating PD-L1 negative tumors comprising administering fusion proteins comprising a CD80 ECD and a Fc domain of human IgG1.

In certain aspects, a method of treating a PD-L1 negative tumor in a subject comprises administering to the subject a composition comprising CD80 extracellular domain (ECD) fusion molecules. In certain aspects, the tumor has been determined to be PD-L1 negative prior to the administration. In certain aspects, the method further comprises determining that the tumor is PD-L1 negative prior to the administration.

In certain aspects, a method of selecting a subject with a tumor for treatment with a composition comprising CD80 ECD fusion molecules comprises determining whether a tumor sample obtained from the subject is PD-L1 negative and selecting the subject for treatment with the composition if the tumor sample is determined to be PD-L1 negative.

In certain aspects, a composition comprising CD80 ECD fusion molecules is for use in the treatment of a PD-L1 negative cancer tumor in a subject. In certain aspects of the composition for use, the subject is selected for the treatment by determining that a tumor sample obtained from the subject is PD-L1 negative.

In certain aspects, a composition comprising CD80 ECD fusion molecules is for use in the treatment of a tumor in a subject, wherein the tumor has been determined to be PD-L1 negative.

In certain aspects, an in vitro method for identifying a subject with a tumor that is responsive to treatment with a composition comprising CD80 ECD fusion molecules comprises determining whether a tumor sample obtained from the subject is PD-L1 negative, wherein the subject is identified as being responsive to treatment with a CD80 ECD fusion molecule if the tumor sample is determined to be PD-L1 negative.

In certain aspects, an vitro use of at least one agent capable of determining that a tumor sample is PD-L1 negative is for identifying a subject with a tumor that is responsive to treatment with a composition comprising CD80 ECD fusion molecules.

In certain aspects of a method, composition, or use provided herein, the tumor has been determined or is determined to be PD-L1 negative using an agent that is capable of detecting PD-L1 protein. In certain aspects, the agent is an antibody that specifically binds to PD-L1 protein. In certain aspects, the tumor has been determined or is determined to be PD-L1 negative by Western blot. In certain aspects, the tumor has been determined or is determined to be PD-L1 negative by fluorescence-activated cell sorting (FACS). In certain aspects, the tumor has been determined or is determined to be PD-L1 negative by immunohistochemistry (IHC). In certain aspects, the sample is a paraffin-embedded sample.

In certain aspects, of a method, composition, or use provided herein, the tumor has been determined or is determined to be PD-L1 negative using an agent that is capable of detecting PD-L1 mRNA. In certain aspects, the tumor has been determined or is determined to be PD-L1 negative by quantitative reverse transcriptase (RT)-polymerase chain reaction (PCR). In certain aspects, the tumor has been determined or is determined to be PD-L1 negative using RNA-Seq. In certain aspects, the tumor has been determined or is determined to be PD-L1 negative using a microarray.

In certain aspects of a method, composition, or use provided herein, the tumor is a solid tumor. In certain aspects of a method, composition, or use provided herein, the subject is afflicted with a cancer selected from the group consisting of colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer. In certain aspects of a method, composition, or use provided herein, the subject is afflicted with a cancer that is recurrent or progressive after a therapy consisting of surgery, chemotherapy, radiation therapy, or a combination thereof.

In certain aspects of a method, composition, or use provided herein, the CD80 ECD fusion molecules comprise a human CD80 ECD and a human IgG1 Fc domain.

In certain aspects of a method, composition, or use provided herein, the composition comprises sialylated CD80 ECD fusion molecules. In certain aspects, the sialylated CD80 ECD fusion molecules comprise at least 15 moles of sialic acid (SA) per mole of fusion protein. In certain aspects, the sialylated CD80 ECD fusion molecules comprise 15-60 moles of SA per mole of fusion protein. In certain aspects, the sialylated CD80 ECD fusion molecules comprise 15-40 moles of SA per mole of fusion protein. In certain aspects, the sialylated CD80 ECD fusion molecules comprise 15-30 moles of SA per mole of fusion protein. In certain aspects, the sialylated CD80 ECD fusion molecules comprise 20-30 moles of SA per mole of fusion protein.

In certain aspects of a method, composition, or use provided herein, the CD80 ECD fusion molecules comprise a human CD80 ECD comprising the amino acid sequence of SEQ ID NO:1. In certain aspects of a method, composition, or use provided herein, the CD80 ECD fusion molecules comprise a human IgG1 Fc domain comprising the amino acid sequence of SEQ ID NO:3. In certain aspects of a method, composition, or use provided herein, the Fc domain of human IgG1 is linked to the carboxy terminus of the ECD of human CD80. In certain aspects, of a method, composition, or use provided herein, the CD80 ECD fusion molecules comprise the amino acid sequence of SEQ ID NO:5.

In certain aspects of a method, composition, or use provided herein the PD-L1 negative tumor has a TPS score of less than 5% or less than 1%.

In certain aspects of a method, composition, or use provided herein the composition alone does not cause significant release of interferon gamma or TNF alpha from T-cells in vitro. In certain aspects of a method, composition, or use provided herein, the composition alone causes less release of interferon gamma or TNF alpha from T-cells in vitro than TGN1412 alone. In certain aspects of a method, composition, or use provided herein, the composition alone is at least 1000-fold less potent at inducing interferon gamma or TNF alpha release compared to TGN1412 alone. In certain aspects of a method, composition, or provided herein, the composition is capable of at least 90% tumor growth inhibition in at least one mouse syngeneic cancer model over a period of at least one week, 10 days, two weeks, or three weeks following administration of a single dose of the composition at 0.3 to 0.6 mg/kg. In certain aspects, the mouse syngeneic cancer model is a CT26 tumor model.

In certain aspects of a method, composition, or use of provided herein, the treatment comprises administration of about 0.07 mg to about 70 mg of the CD80 ECD fusion molecules. In certain aspects, the treatment comprises administration of about 7.0 mg to about 70 mg of the CD80 ECD fusion molecules. In certain aspects, the treatment comprises administration of about 70 mg of the CD80 ECD fusion molecules. In certain aspects, the treatment comprises administration of about 42 mg of the CD80 ECD fusion molecules. In certain aspects, the treatment comprises administration of about 21 mg of the CD80 ECD fusion molecules. In certain aspects, the treatment comprises administration of about 7 mg of the CD80 ECD fusion molecules. In certain aspects, the treatment comprises administration of about 2.1 mg of the CD80 ECD fusion molecules. In certain aspects, the treatment comprises administration of about 0.7 mg of the CD80 ECD fusion molecules. In certain aspects, the treatment comprises administration of about 0.21 mg of the CD80 ECD fusion molecules. In certain aspects, the treatment comprises administration of about 0.07 mg of the CD80 ECD fusion molecules.

In certain aspects of a method, composition, or use provided herein, the treatment comprises administration once every three weeks.

In certain aspects of a method, composition, or use provided herein, the treatment comprises intravenous administration of the CD80 ECD fusion molecules.

In certain aspects of a method, composition, or use provided herein, the subject has not received prior therapy with a PD-1/PD-L1 antagonist.

In certain aspects of a method, composition, or use provided herein, the subject has received prior therapy with at least one anti-angiogenic agent. In certain aspects, the anti-angiogenic agent is sunitinib, sorafenib, pazopanib, axitinib, tivozanib, ramucirumab, or bevacizumab. In certain aspects, the anti-angiogenic agent was administered in an advanced or metastatic setting.

In certain aspects of a method, composition, or use provided herein, the subject is afflicted with a melanoma that has a BRAF mutation. In certain aspects, the subject has received prior therapy with at least one BRAF inhibitor. In certain aspects, the BRAF inhibitor is vemurafenib or dabrafenib. In certain aspects, the BRAF inhibitor was administered in an advanced or metastatic setting.

In certain aspects of a method, composition, or use provided herein, the tumor is recurrent or progressive after a therapy selected from surgery, chemotherapy, radiation therapy, and a combination thereof In certain aspects, a method of treating a PD-L1 negative tumor in a human patient, comprises administering to the patient a composition comprising about 0.07 mg to about 70 mg CD80 extracellular domain (ECD) fusion molecules comprising the amino acid sequence of SEQ ID NO:5. In certain aspects, the tumor has been determined to be PD-L1 negative by IHC prior to the administration. In certain aspects, the composition comprises sialylated CD80 ECD fusion molecules and the sialylated CD80 ECD fusion molecules comprise 15-60 moles of SA per mole of fusion protein.

BRIEF DESCRIPTION OF THE DRAWINGS

FIGS. 3A and 3B: PBMCs were evaluated for hCD8-Fc engagement and receptor occupancy. (A) Peripheral immune cell subsets were identified as B cells (CD19+), Monocytes (CD14+), NK cells (CD56+CD3−), and T cells (CD56−CD3+ and CD4+ or CD8+) by flow cytometry. Representative flow cytometry plots depict the gating strategy. (B) Increasing concentrations of hCD80-Fc were incubated with PBMCs, and hCD80-Fc engagement was measured both via biotin-labeled anti-hIgG-Fc followed by streptavidin Alexa488 ("bound drug") and by detection of CD80 ligands with competing Ab clones ("free" PD-L1 or CD28) enumerated as Antibody Binding Capacity (ABC) values. CTLA-4 was not detected on any immune cell evaluated (data not shown). L.D., limit of detection of ABC. Graphs depict mean±SD of n=3 donors. ANOVA-based statistical testing was performed for drug concentrations against no drug (0 µg/mL) where $*p<0.05$, $p<0.01$, $*p<0.001$ was considered significant. (See Example 2.)

Figure 1A:
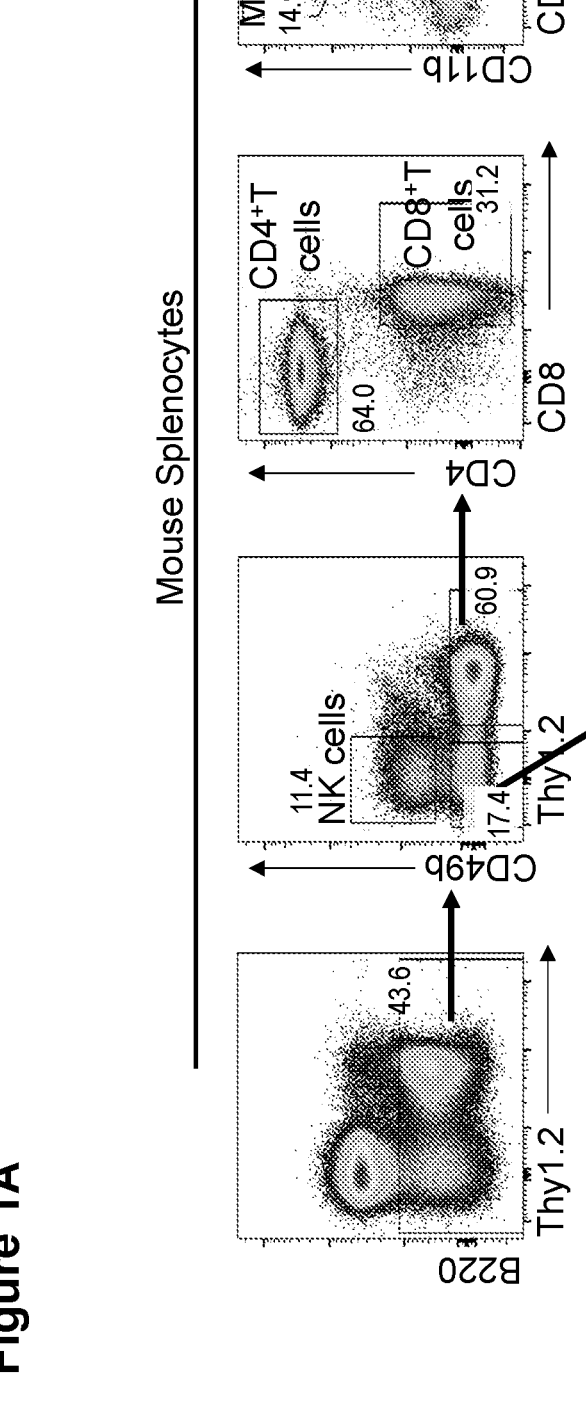
FIGS. 1A and 1B: Mouse splenocytes were evaluated for mCD80-Fc engagement and receptor occupancy. (A) Splenic immune cell subsets were identified as CD11b+ DCs (B220-Thy1.2−CD49b−CD11c+CD11b+), CD11b− DCs (B220− Thy1.2−CD49b-CD11c+CD11b−), Macrophages (B220−Thy1.2−CD49b−CD11c−CD11b+), NK cells (B220− Thy1.2−CD49b+), and T cells (CD3+CD4+ or CD3+CD8+) by flow cytometry. Representative flow cytometry plots depict the gating strategy. (B) Increasing concentrations of mCD80-Fc were incubated with mouse spleno-cytes (BALB/c strain top row; C57Bl/6 strain bottom row), and mCD80-Fc engagement was measured both via biotin-labeled anti-mIgG followed by streptavidin Alexa488 ("bound drug") and by detection of CD80 ligands with competing Ab clones ("free" PD-L1 or CD28) enumerated as Antibody Binding Capacity (ABC) values. CTLA-4 was not detected on any immune cell evaluated (data not shown). L.D., limit of detection of ABC. Graphs depict mean±SD of n=3 animals/strain measured in technical duplicates. ANOVA-based statistical testing was performed for drug concentrations against no drug (0 µg/mL) where $*p<0.05$, $p<0.01$, $*p<0.001$, $****p<0.0001$ was considered significant. (See Example 1.)

DESCRIPTION OF PARTICULAR
EMBODIMENTS 1. Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The terms "polypeptide," "peptide," and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "fusion molecule" as used herein refers to a molecule composed of two or more different molecules that do not occur together in nature being covalently or noncovalently joined to form a new molecule. For example, fusion molecules may be comprised of a polypeptide and a polymer such as PEG, or of two different polypeptides. A "fusion protein" refers to a fusion molecule composed of two or more polypeptides that do not occur in a single molecule in nature.

A "CD80 extracellular domain" or "CD80 ECD" refers to an extracellular domain polypeptide of CD80, including natural and engineered variants thereof. A CD80 ECD can, for example, comprise, consist essentially of, or consist of the amino acid sequence set forth in SEQ ID NO:1 or 2. A "CD80 ECD fusion molecule" refers to a molecule comprising a CD80 ECD and a fusion partner. The fusion partner may be covalently attached, for example, to the N- or C-terminal of the CD80 ECD or at an internal location. A "CD80 ECD fusion protein" is a CD80 ECD fusion molecule comprising a CD80 ECD and another polypeptide that is not naturally associated with the CD80 ECD, such as an Fc domain. A CD80 ECD fusion protein can, for example, comprise, consist essentially of, or consist of the amino acid sequence set forth in SEQ ID NO: 4 or 5.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "cancer" is used herein to refer to a group of cells that exhibit abnormally high levels of proliferation and growth. A cancer can be a solid tumor, for example, a colorectal cancer, breast cancer, gastric cancer, non-small cell lung cancer, small cell lung cancer, melanoma, squamous cell carcinoma of the head and neck, ovarian cancer, pancreatic cancer, renal cell carcinoma, hepatocellular carcinoma, bladder cancer, or endometrial cancer.

Terms such as "treating," "treatment," and "to treat," refer to therapeutic measures that cure, slow down, lessen symptoms of, and/or halt progression of a pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), overall survival (OS), complete response (CR), partial response (PR), stable disease (SD), a decrease in progressive disease (PD), a reduced time to progression (TTP), or any combination thereof.

The terms "administer," "administering," "administration," and the like, as used herein, refer to methods that may be used to enable delivery of a drug, e.g., a CD80 ECD fusion protein to the desired site of biological action (e.g., intravenous administration). Administration techniques that can be employed with the agents and methods described herein are found in e.g., Goodman and Gilman, *The Pharmacological Basis of Therapeutics,* current edition, Pergamon; and Remington's, *Pharmaceutical Sciences,* current edition, Mack Publishing Co., Easton, Pa.

The term "therapeutically effective amount" refers to an amount of a drug, e.g., a CD80 ECD fusion protein, effective to treat a disease or disorder in a subject. In the case of cancer, the therapeutically effective amount of the drug can reduce the number of cancer cells; reduce the tumor size or burden; inhibit, to some extent, cancer cell infiltration into peripheral organs; inhibit, to some extent, tumor metastasis; inhibit, to some extent, tumor growth; relieve, to some extent, one or more of the symptoms associated with the cancer; and/or result in a favorable response such as increased progression-free survival (PFS), disease-free survival (DFS), overall survival (OS), complete response (CR), partial response (PR), or, in some cases, stable disease (SD), a decrease in progressive disease (PD), a reduced time to progression (TTP), or any combination thereof.

The terms "resistant" or "nonresponsive" when used in the context of treatment with a therapeutic agent, means that the subject shows decreased response or lack of response to a standard dose of the therapeutic agent, relative to the subject's response to the standard dose of the therapeutic agent in the past, or relative to the expected response of a similar subject with a similar disorder to the standard dose of the therapeutic agent. Thus, in some embodiments, a subject may be resistant to a therapeutic agent although the subject has not previously been given the therapeutic agent, or the subject may develop resistance to the therapeutic agent after having responded to the agent on one or more previous occasions.

A "refractory" cancer is one that progresses even though an anti-tumor treatment, such as a chemotherapy, is administered to the cancer patient.

A "recurrent" cancer is one that has regrown, either at the initial site or at a distant site, after a response to initial therapy.

The terms "programmed cell death 1 ligand 1" and "PD-L1" refer to one of two cell surface glycoprotein ligands for PD-1 (the other being PD-L2) that down regulate T-cell activation and cytokine secretion upon binding to PD-1. The term "PD-L1" as used herein includes human PD-L1 (hPD-L1), naturally occurring variants and isoforms of hPD-1, and species homologs of hPD-L1. A mature hPD-L1 sequence is provided as SEQ ID NO:6.

The term "PD-L1 negative tumor" refers to a tumor that does not significantly express PD-L1 on the cell surface. The presence or absence of PD-L1 can be determined, for example, using immunohistochemistry, which can be quantitated using a tumor proportion score (TPS). A TPS (%) is equal to [Number of PD-L1-stained tumor cells/total number of viable tumor cells]×100. Accordingly, a PD-L1 negative tumor can be a tumor with a TPS score of less than 5% or less than 1%.

The term "PD-1/PD-L1 antagonist" refers to a moiety that disrupts the PD-1/PD-L1 signaling pathway. In some embodiments, the antagonist inhibits the PD-1/PD-L1 signaling pathway by binding to PD-1 and/or PD-L1. In some embodiments, the PD-1/PD-L1 antagonist also binds to PD-L2. In some embodiments, a PD-1/PD-L1 antagonist blocks binding of PD-1 to PD-L1 and optionally PD-L2. Nonlimiting exemplary PD-1/PD-L1 antagonists include PD-1 antagonists, such as antibodies that bind to PD-1 (e.g., nivolumab and pembrolizumab); PD-L1 antagonists, such as antibodies that bind to PD-L1 (e.g., atezolizumab, durvalumab and avelumab); fusion proteins, such as AMP-224; and peptides, such as AUR-012.

An "anti-angiogenic agent" or "angiogenesis inhibitor" refers to an agent such as a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that an anti-angiogenic agent includes those agents that bind and block the angiogenic activity of the angiogenic factor or its receptor. For example, an anti-angiogenic agent is an antibody to or other antagonist of an angiogenic agent, e.g., antibodies to VEGF-A (e.g., bevacizumab)) (Avastin®)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12):1359-1364; Tonini et al. (2003) *Oncogene* 22:6549-6556 (e.g., Table 2 listing known anti-angiogenic factors); Sato (2003) *Int. J. Clin. Oncol.* 8:200-206 (e.g., Table 1 listing anti-angiogenic agents used in clinical trials), and Jayson (2016) *Lancet* 338(10043):518-529.

The term "pharmaceutical composition" refers to a preparation which is in such form as to permit the biological activity of the active ingredient to be effective, and which contains no additional components which are unacceptably toxic to a subject to which the formulation would be administered. The formulation can be sterile. A pharmaceutical composition may contain a "pharmaceutical carrier," which refers to carrier that is non-toxic to recipients at the dosages and concentrations employed and is compatible with other ingredients of the formulation. The pharmaceutically acceptable carrier is appropriate for the formulation employed. For example, if the therapeutic agent is to be administered intravenously, the carrier ideally is not irritable to the skin and does not cause injection site reaction.

As used herein, the terms "about" and "approximately," when used to modify a numeric value or numeric range, indicate that deviations of 5% to 10% above and 5% to 10% below the value or range remain within the intended meaning of the recited value or range.

Any compositions or methods provided herein can be combined with one or more of any of the other compositions and methods provided herein.

2. CD80 Extracellular Domain Fc Fusion Proteins

Provided herein are methods of administering CD80 ECD fusion proteins comprising a CD80 ECD and an Fc domain (a "CD80 ECD Fc fusion protein"). Exemplary CD80 ECD fusion proteins are provided, for example, in WO 2017/079117, which is herein incorporated by reference in its entirety.

The CD80 ECD can, for example, be a human CD80 ECD. In certain aspects, the human CD80 ECD comprises, consists essentially of, or consists of the amino acid sequence set forth in SEQ ID NO:1.

The Fc domain can be the Fc domain of an IgG. The Fc domain can be the Fc domain of a human immunoglobulin. In certain aspects, the Fc domain is a human IgG Fc domain. In certain aspects, the Fc domain is a human IgG1 Fc domain. In certain aspects, the human IgG1 Fc domain comprises, consists essentially of, or consists of the amino acid sequence set forth in SEQ ID NO:4.

The CD80 ECD and the Fc domain can be directly linked such that the N-terminal amino acid of the Fc domain immediately follows the C-terminal amino acid of the CD80 ECD. In certain aspects, the CD80 ECD and the Fc domain are translated as a single polypeptide from a coding sequence that encodes both the CD80 ECD and the Fc domain. In certain aspects, the CD80 ECD Fc fusion protein comprises a human CD80 ECD and a human IgG1 Fc domain. In certain aspects, the CD80 ECD Fc fusion protein comprises, consists essentially of, or consists of the amino acid sequence set forth in SEQ ID NO:5.

CD80 ECD Fc fusion proteins can, depending on how they are produced, have different levels of particular glycosylation modifications. For example, a CD80 ECD Fc fusion protein can be sialylated and can have different amounts of sialic acid (SA) residues.

In certain aspects, a CD80 ECD Fc fusion protein (e.g., comprising a human CD80 ECD and a human IgG1 Fc domain, or comprising SEQ ID NO:5) comprises 10 to 60 molecules of SA. In certain aspects, a CD80 ECD Fc fusion protein (e.g., comprising a human CD80 ECD and a human IgG1 Fc domain, or comprising SEQ ID NO:5) comprises 15 to 60 molecules of SA. In certain aspects, a CD80 ECD Fc fusion protein (e.g., comprising a human CD80 ECD and a human IgG1 Fc domain, or comprising SEQ ID NO:5) comprises 10 to 40 molecules of SA. In certain aspects, a CD80 ECD Fc fusion protein (e.g., comprising a human CD80 ECD and a human IgG1 Fc domain, or comprising SEQ ID NO:5) comprises 15 to 30 molecules of SA. In certain aspects, a CD80 ECD Fc fusion protein (e.g., comprising a human CD80 ECD and a human IgG1 Fc domain, or comprising SEQ ID NO:5) comprises 15 to 25 molecules of SA. In certain aspects, a CD80 ECD Fc fusion protein (e.g., comprising a human CD80 ECD and a human IgG1 Fc domain, or comprising SEQ ID NO:5) comprises 20 to 40 molecules of SA. In certain aspects, a CD80 ECD Fc fusion protein (e.g., comprising a human CD80 ECD and a human IgG1 Fc domain, or comprising SEQ ID NO:5) comprises 20 to 30 molecules of SA. In certain aspects, a CD80 ECD Fc fusion protein (e.g., comprising a human CD80 ECD and a human IgG1 Fc domain, or comprising SEQ ID NO:5) comprises 30 to 40 molecules of SA. In certain aspects, a CD80 ECD Fc fusion protein (e.g., comprising a human CD80 ECD and a human IgG1 Fc domain, or comprising SEQ ID NO:5) comprises 10, 15, 20, 25, 30, 35, or 40 molecules of SA. In certain aspects, a CD80 ECD Fc fusion protein (e.g., comprising a human CD80 ECD and a human IgG1 Fc domain, or comprising SEQ ID NO:5) comprises at least 15 molecules of SA. In certain aspects, a CD80 ECD Fc fusion protein (e.g., comprising a human CD80 ECD and a human IgG1 Fc domain, or comprising SEQ ID NO:5) comprises at least 20 molecules of SA. In certain aspects, a CD80 ECD Fc fusion protein (e.g., comprising a human CD80 ECD and a human IgG1 Fc domain, or comprising SEQ ID NO:5) comprises at least 25 molecules of SA. In certain aspects, a CD80 ECD Fc fusion protein (e.g., comprising a human CD80 ECD and a human IgG1 Fc domain, or comprising SEQ ID NO:5) comprises at least 30 molecules of SA. In certain aspects, a CD80 ECD Fc fusion protein (e.g., comprising a human CD80 ECD and a human IgG1 Fc domain, or comprising SEQ ID NO:5) comprises at least 35 molecules of SA. In certain aspects, a CD80 ECD Fc fusion protein (e.g., comprising a human CD80 ECD and a human IgG1 Fc domain, or comprising SEQ ID NO:5) comprises at least 40 molecules of SA.

3. Pharmaceutical Compositions Comprising CD80 Extracellular Domain Fc Fusion Proteins Provided herein are methods of administering pharmaceutical compositions comprising CD80 ECD Fc fusion proteins, e.g. having the desired degree of purity in a physiologically acceptable carrier, excipient, or stabilizer (Remington's Pharmaceutical Sciences (1990) Mack Publishing Co., Easton, PA). Acceptable carriers, excipients, or stabilizers are nontoxic to recipients at the dosages and concentrations employed. (See, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). The compositions to be used for in vivo administration can be sterile. This is readily accomplished by filtration through, e.g., sterile filtration membranes.

In certain aspects, a pharmaceutical composition comprising a CD80 ECD Fc fusion protein (e.g. comprising a human CD80 ECD and a human IgG1 Fc domain, or comprising SEQ ID NO:5) is formulated for intravenous administration.

In certain aspects, a pharmaceutical composition comprises 70 mg of a CD80 ECD Fc fusion protein (e.g. comprising a human CD80 ECD and a human IgG1 Fc domain, or comprising SEQ ID NO:5). In certain aspects, a pharmaceutical composition comprises 42 mg of a CD80 ECD Fc fusion protein (e.g. comprising a human CD80 ECD and a human IgG1 Fc domain, or comprising SEQ ID NO:5). In certain aspects, a pharmaceutical composition comprises 21 mg of a CD80 ECD Fc fusion protein (e.g. comprising a human CD80 ECD and a human IgG1 Fc domain, or comprising SEQ ID NO:5). In certain aspects, a pharmaceutical composition comprises 7 mg of a CD80 ECD Fc fusion protein (e.g. comprising a human CD80 ECD and a human IgG1 Fc domain, or comprising SEQ ID NO:5). In certain aspects, a pharmaceutical composition comprises 2.1 mg of a CD80 ECD Fc fusion protein (e.g. comprising a human CD80 ECD and a human IgG1 Fc domain, or comprising SEQ ID NO:5). In certain aspects, a pharmaceutical composition comprises 0.7 mg of a CD80 ECD Fc fusion protein (e.g. comprising a human CD80 ECD and a human IgG1 Fc domain, or comprising SEQ ID NO:5). In certain aspects, a pharmaceutical composition comprises 0.21 mg of a CD80 ECD Fc fusion protein (e.g. comprising a human CD80 ECD and a human IgG1 Fc domain, or comprising SEQ ID NO:5). In certain aspects, a pharmaceutical composition comprises 0.07 mg of a CD80 ECD Fc fusion protein (e.g. comprising a human CD80 ECD and a human IgG1 Fc domain, or comprising SEQ ID NO:5).

In certain aspects, a pharmaceutical composition comprises 0.07 to 70 mg of a CD80 ECD Fc fusion protein (e.g. comprising a human CD80 ECD and a human IgG1 Fc domain, or comprising SEQ ID NO:5). In certain aspects, a pharmaceutical composition comprises 7 to 70 mg of a CD80 ECD Fc fusion protein (e.g. comprising a human CD80 ECD and a human IgG1 Fc domain, or comprising SEQ ID NO:5).

In certain aspects a pharmaceutical composition comprises CD80 ECD Fc fusion proteins (e.g. comprising a human CD80 ECD and a human IgG1 Fc domain, or comprising SEQ ID NO:5) comprising 10 to 60 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 15 to 60 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 10 to 40 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 15 to 30 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 15 to 25 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 20 to 40 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 20 to 30 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 30 to 40 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising 10, 15, 20, 25, 30, 35, or 40 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising at least 15 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising at least 20 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising at least 25 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising at least 30 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising at least 35 moles of SA per mole CD80 ECD Fc fusion protein. In certain aspects a pharmaceutical composition comprises CD80 ECD Fc fusion proteins (e.g. comprising a human CD80 ECD and a human IgG1 Fc domain, or comprising SEQ ID NO:5) comprising at least 40 moles of SA per mole CD80 ECD Fc fusion protein.

4. Methods and Uses of CD80 Extracellular Domain Fc Fusion Proteins

Presented herein are methods for treating a PD-L1 negative tumor (e.g., in a human) comprising administering to a subject in need thereof a CD80 ECD Fc fusion protein, or a pharmaceutical composition thereof. The CD80 ECD Fc fusion protein can comprise the extracellular domain of human CD80 and the Fc domain of human IgG1. In some embodiments, the CD80 ECD Fc fusion protein comprises the sequence of SEQ ID NO:5.

The presence or absence of PD-L1 can be determined using an agent that is capable of detecting PD-L1 protein, such as an anti-PD-L1 antibody. Thus, in some embodiments, a tumor can be identified as a PD-L1 negative tumor by subjecting a tumor sample to Western blot, fluorescence-activated cell sorting (FACS), or immunohistochemistry (IHC) using such an agent.

In some embodiments, IHC can be used to quantitate the amount of PD-L1 in a tumor sample, using for example, a tumor proportion score (TPS). A TPS (%) is equal to [Number of PD-L1-stained tumor cells/total number of viable tumor cells]×100. As provided herein, a PD-L1 negative tumor can be a tumor with a TPS score of less than 5%. As provided herein, a PD-L1 negative tumor can be a tumor with a TPS score of less than 1%.

The presence or absence of PD-L1 can be determined using an agent that is capable of detecting PD-L1 mRNA. Thus, in some embodiments, a tumor can be identified as a PD-L1 negative tumor by subjecting a tumor sample to quantitative reverse transcriptase (RT)-polymerase chain reaction (PCR), RNA-Seq, or microarray.

In one aspect, a method of treating a PD-L1 negative tumor in a patient comprises administering to the patient about 70 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 42 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 21 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 7 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 2.1 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 0.7 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 0.21 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 0.07 mg of a CD80 ECD fusion protein (e.g., comprising the amino acid sequence set forth in SEQ ID NO:5) e.g., once every three weeks.

In one aspect, a method of treating a PD-L1 negative tumor in a patient comprises administering to the patient 70 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 42 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 21 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 7 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 2.1 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 0.7 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 0.21 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient 0.07 mg of a CD80 ECD fusion protein (e.g., comprising the amino acid sequence set forth in SEQ ID NO:5) e.g., once every three weeks.

In one aspect, a method of treating a PD-L1 negative tumor in a patient comprises administering to the patient about 0.07 mg to about 70 mg of a CD80 ECD fusion protein (e.g., comprising the amino acid sequence set forth in SEQ ID NO:5) e.g., once every three weeks. In one aspect, a method of treating a PD-L1 negative tumor in a patient comprises administering to the patient about 7 mg to about 70 mg of a CD80 ECD fusion protein (e.g., comprising the amino acid sequence set forth in SEQ ID NO:5) e.g., once every three weeks.

According to the methods provided herein, a of a CD80 ECD fusion protein (e.g., comprising the amino acid sequence set forth in SEQ ID NO:5) can be administered intravenously.

According to the methods provided herein, the PD-L1 negative tumor can be, for example a solid tumor, including e.g., an advanced or metastatic solid tumor. In certain instances, the PD-L1 negative tumor is not a primary central nervous system tumor.

In certain instances, the PD-L1 negative tumor is a renal cell carcinoma.

In certain instances, the PD-L1 negative tumor is a melanoma.

In certain instances, the PD-L1 negative tumor is a colorectal cancer, breast cancer, gastric cancer, non-small cell lung cancer, small cell lung cancer, melanoma, squamous cell carcinoma of the head and neck, ovarian cancer, pancreatic cancer, renal cell carcinoma, hepatocellular carcinoma, bladder cancer, or endometrial cancer.

The patient to be treated according to the methods provided herein may have received prior therapy with at least one PD-1/PD-L1 antagonist selected from a PD-1 antagonist and a PD-L1 antagonist. The PD-1/PD-L1 antagonist can be, for example, nivolumab, pembrolizumab, atezolizumab, durvalumab, or avelumab. The PD-1/PDL-1 antagonist may have been administered in an advanced or metastatic setting. In some embodiments, the tumor is non-responsive to such treatment or recurrent during or after such treatment. In other instances, the patient to be treated according to the methods provided herein has not received prior therapy with a PD-1/PDL-1 antagonist.

The patient to be treated according to the methods provided herein may have received prior therapy with an anti-angiogenic agent. The anti-angiogenic agent can be, for example, sunitinib, sorafenib, pazopanib, axitinib, tivozanib, ramucirumab, or bevacizumab. The anti-angiogenic agent may have been administered in an advanced or metastatic setting.

The patient to be treated according to the methods provided herein, for example a patient with a melanoma, may have a BRAF mutation. The patient may have received prior therapy with a BRAF inhibitor. The BRAF inhibitor can be, for example, vemurafenib and dabrafenib. The BRAF inhibitor may have been administered in an advanced or metastatic setting.

The tumor to be treated according to the methods provided herein can be recurrent or progressive after a therapy selected from surgery, chemotherapy, radiation therapy, and a combination thereof.

The tumor to be treated according to the methods provided herein can be resistant or non-responsive to a PD-1/PD-L1 antagonist, such as nivolumab, pembrolizumab, atezolizumab, durvalumab, or avelumab. The tumor to be treated according to the methods provided herein can be resistant or non-responsive to an anti-angiogenic agent, such as sunitinib, sorafenib, pazopanib, axitinib, tivozanib, ramucirumab, or bevacizumab. The tumor to be treated according to the methods provided herein can be resistant or non-responsive to a BRAF inhibitor, such as vemurafenib or dabrafenib.

The tumor to be treated according to the methods provided herein can be refractory to a PD-1/PD-L1 antagonist, such as nivolumab, pembrolizumab, atezolizumab, durvalumab, or avelumab. The tumor to be treated according to the methods provided herein can be refractory to an anti-angiogenic agent, such as sunitinib, sorafenib, pazopanib, axitinib, tivozanib, ramucirumab, or bevacizumab. The tumor to be treated according to the methods provided herein can be refractory to a BRAF inhibitor, such as vemurafenib or dabrafenib.

The tumor to be treated according to the methods provided herein can be recurrent after treatment with a PD-1/PD-L1 antagonist, such as nivolumab, pembrolizumab, atezolizumab, durvalumab, or avelumab. The tumor to be treated according to the methods provided herein can be recurrent after treatment with an anti-angiogenic agent, such as sunitinib, sorafenib, pazopanib, axitinib, tivozanib, ramucirumab, or bevacizumab. The tumor to be treated according to the methods provided herein can be recurrent after treatment with a BRAF inhibitor, such as vemurafenib or dabrafenib.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Murine CD80 ECD Fusion Molecules (mCD80-Fc) Do Not Engage PD-L1

Adult murine splenocytes from both BALB/c and C57Bl/6 strains were used to determine if a mouse surrogate fusion protein comprising the extracellular domain (ECD) of murine CD80 linked to the Fc domain of mouse IgG2a wild type (mCD80-Fc) engages CD80 ligands.

Mouse splenocytes were prepared from adult BALB/c and C56Bl/6 mice by methods known to those of ordinary skill in the art. The splenocytes ($2\text{-}4\times10^6$ cells/mL) were pelleted by centrifugation and the media discarded. The mCD80-Fc was added at various concentrations (0-1000 μg/mL) and incubated for 40 minutes on ice. Paraformaldehyde (4%) was added to the splenocytes and incubated for 10 minutes at room temperature. The splenocytes were washed and pelleted by centrifugation, followed by addition of biotin-labeled anti-mouse IgG in FACS buffer and further incubation for 20 minutes at room temperature. A mixture of streptavidin-Alexa488 and antibodies directed to CTLA-4, PD-L1, and CD28 were added. Quantum Simply Cellular Bang beads were used to develop a standard curve for mCD80-Fc molecules. Data from the samples was acquired on a BD LSRII or BD LSRFortessa and analyzed using FlowJo, Excel, and Graphpad Prism.

FACS analysis was performed to determine the engagement of mCD80-Fc to CD11b+ dendritic cells, CD11b− dendritic cells, macrophages, NK cells, CD4+ T cells, CD8+ T cells. FIG. 1A shows an example of the gating strategy used in this example.

Figure 1B:
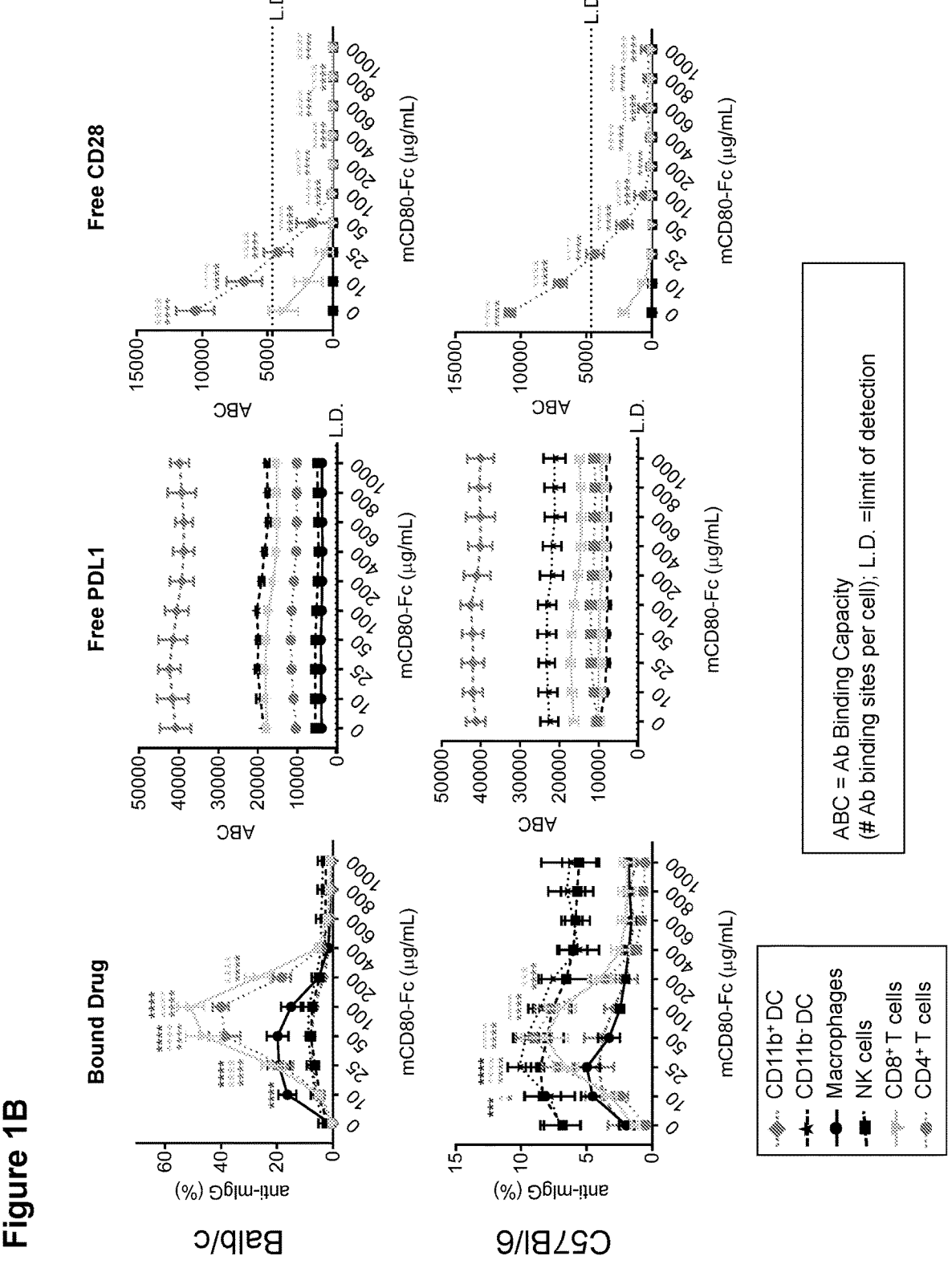

FIG. 1B demonstrates that mCD80-Fc bound, in a concentration-dependent manner, primarily to CD4+ T cells and CD8+ T cells in both types of splenocytes. However, mCD80-Fc did bind a greater proportion of T cells from BALB/c-derived splenocytes than C57Bl/6-derived splenocytes. Additionally, there was a small proportion of mCD80-Fc binding to macrophages in both types of splenocytes. Thus, mCD80-Fc was shown to bind to CD4+ T cells, CD8+ T cells, and macrophages, but does not bind to CD11b+ or CD11b− dendritic cells.

PD-L1 was detected on all immune cells tested, with the highest expression on macrophages. There were no changes in the amount of free PD-L1, even with increasing concentrations of mCD80-Fc, demonstrating that there is no interaction between mCD80-Fc and PD-L1 (FIG. 1B).

In contrast, CD4+ and CD8+ T cells are the only immune cells evaluated that displayed CD28 expression. With increasing concentrations of mCD80-Fc, there was a significant decrease in the amount of free CD28, demonstrating that mCD80-Fc binds to CD28 (FIG. 1B). CTLA-4 was not detected on any immune cell types evaluated.

These results demonstrate that mCD80-Fc primarily binds CD4+ T cells and CD8+ T cells from BALB/c and C57Bl/6 splenocytes via CD28 engagement, and not PD-L1 engagement.

Example 2: Human CD80 ECD Fusion Molecules (hCD80-Fc) do not Engage PD-L1

Chinese Hamster Ovary ("CHO") cells were evaluated for hCD80-Fc engagement of human CD80 ligands. CHO cells were engineered to express human CTLA-4, PD-L1, CD28, or all three CD80 ligands (i.e., CHO-CTLA4/PD-L1/CD28; "CHO-3"). The protocol for determining hCD80-Fc engagement to ligands is the same as was performed in Example 1.

Figure 2A:
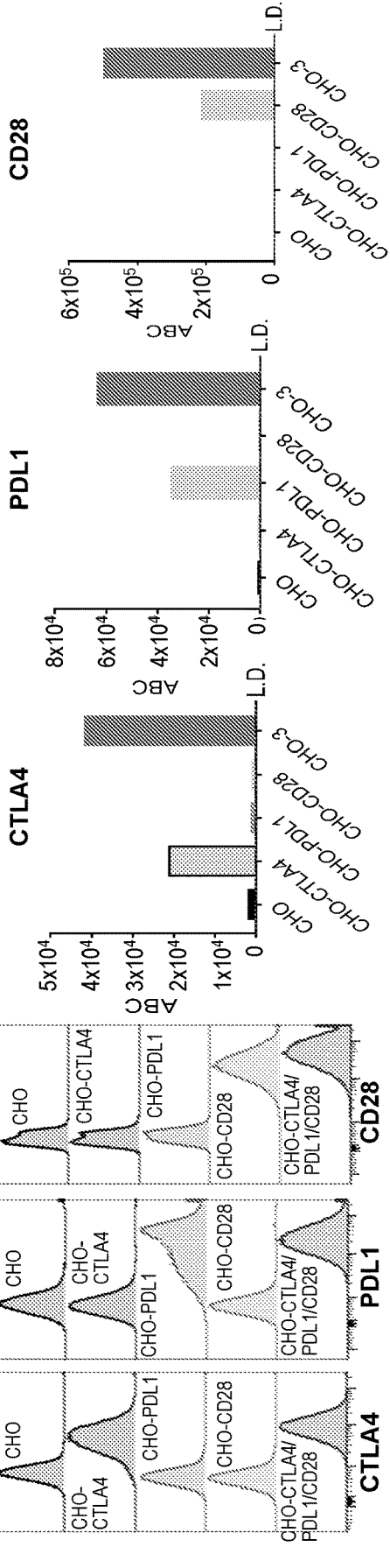
FIGS. 2A and 2B: hCD80-Fc receptor occupancy experiments were performed on lentivirally-transduced CHO cells expressing human CTLA-4, PD-L1, CD28, or all three CD80 ligands (CHO-CTLA4/PDL1/CD28; "CHO-3"). Parental, non-transduced CHO cells were used as a negative control. (A) CD80 ligand expression was evaluated in CHO cell lines by flow cytometry. Representative staggered histograms are shown, and Antibody Binding Capacity (ABC) values to determine the number of Ab binding sites per cell are enumerated in bar graphs to the right. (B) CHO cells were incubated with increasing concentrations of hCD80-Fc (solid shapes) or hIgGI-Fc control (open shapes). hCD80-Fc binding was detected both via biotin-labeled anti-hIgG-Fc followed by streptavidin BV605 ("bound drug") and by detection of CD80 ligands with competing Ab clones ("free" CTLA-4, PD-L1, CD28). L.D., limit of detection of ABC. Graphs depict mean±SEM from technical replicates. ANOVA-based statistical testing was performed for drug concentrations against no drug (0 µg/mL) where $*p<0.05$, $p<0.01$, $*p<0.001$ was considered significant. (See Example 2.)
Figure 2B:
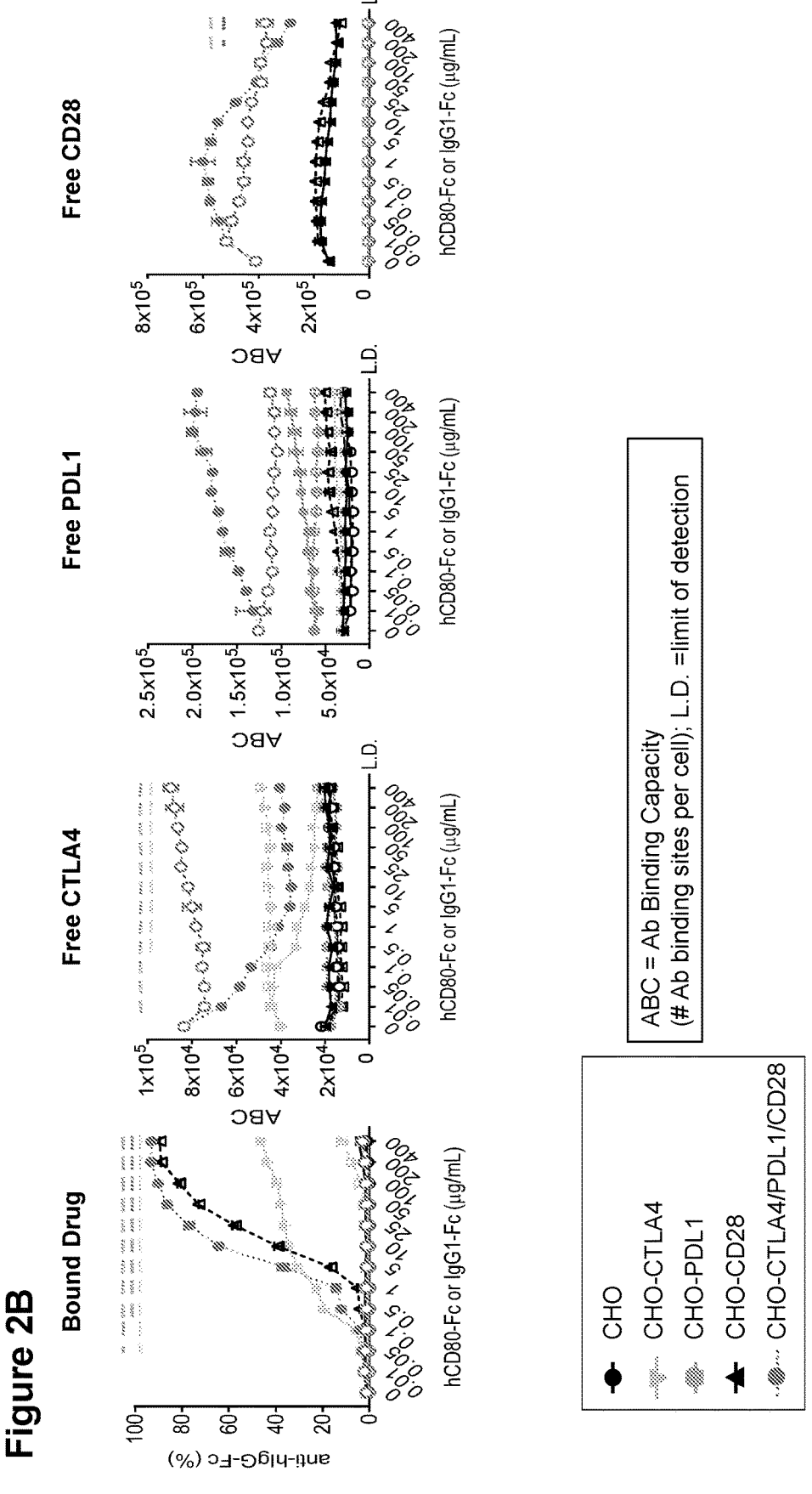

FIG. 2A shows CD80 ligand expression in all CHO cell lines by flow cytometry. Representative staggered histograms are shown and Antibody Binding Capacity (ABC) values to determine the number of Ab binding sites per cell are enumerated in bar graphs to the right. FIG. 2B shows hCD80-Fc bound CHO-CTLA4, CHO-CD28, and CHO-3 cells in a concentration-dependent manner, with hCD80-Fc binding to CD80 ligands at as low as 0.5 µg/mL. Moreover, the binding of hCD80-Fc to the CD80 ligands caused a decrease in free CTLA-4 and CD28 in the respective cell lines (FIG. 2B). However, hCD80-Fc did not bind to CHO-PD-L1 or parental CHO cells, which demonstrates that hCD80-Fc does not engage PD-L1.

These results show that hCD80-Fc engages CTLA-4 and CD28, but not PD-L1. With respect to the CHO-3 cell line, hCD80-Fc bound both CTLA-4 and CD28 at similar levels as in the singly-expressing CHO cell lines.

Figure 3A:
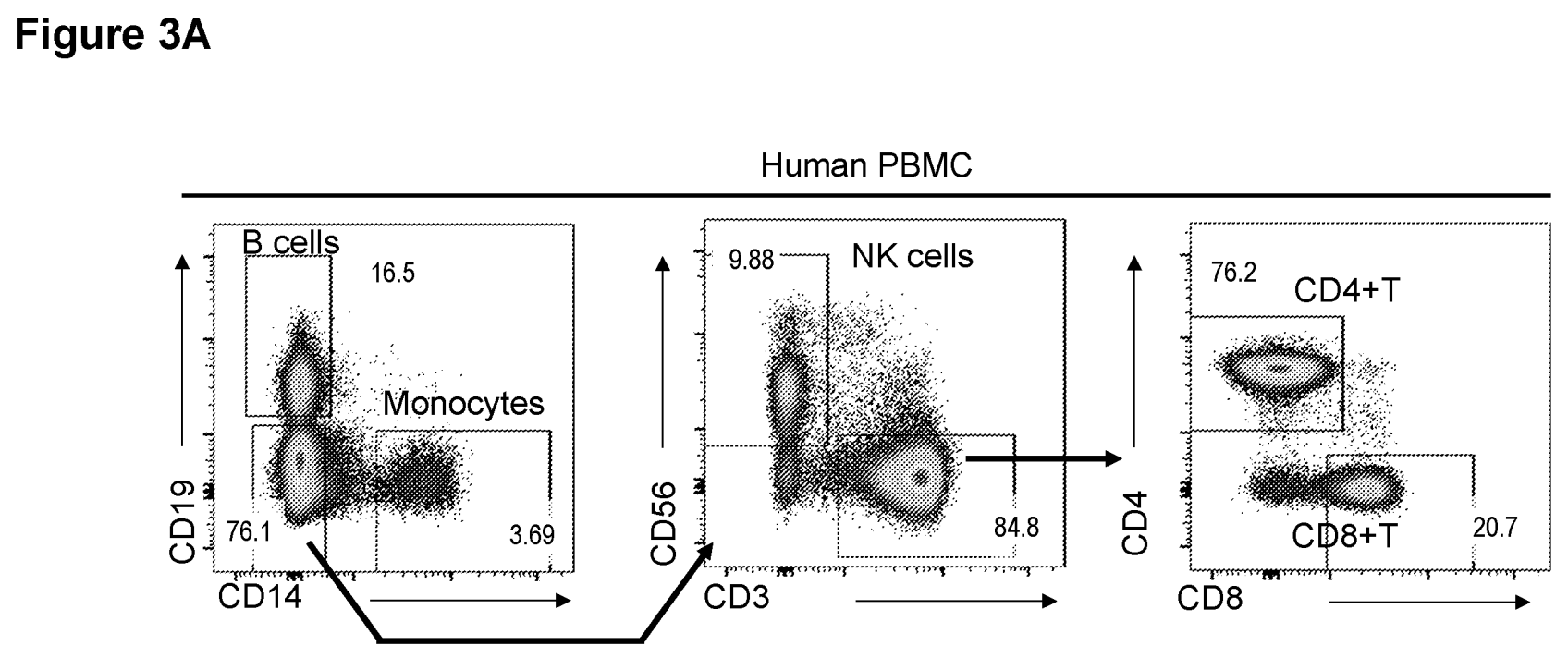

Human PBMCs were evaluated for hCD80-Fc engagement on B cells (CD19+), monocytes (CD14+), NK cells (CD56+), and T cells (CD3+CD4+ or CD3+CD8+). FIG. 3A demonstrates an example FACS gating strategy for this study.

Figure 3B:
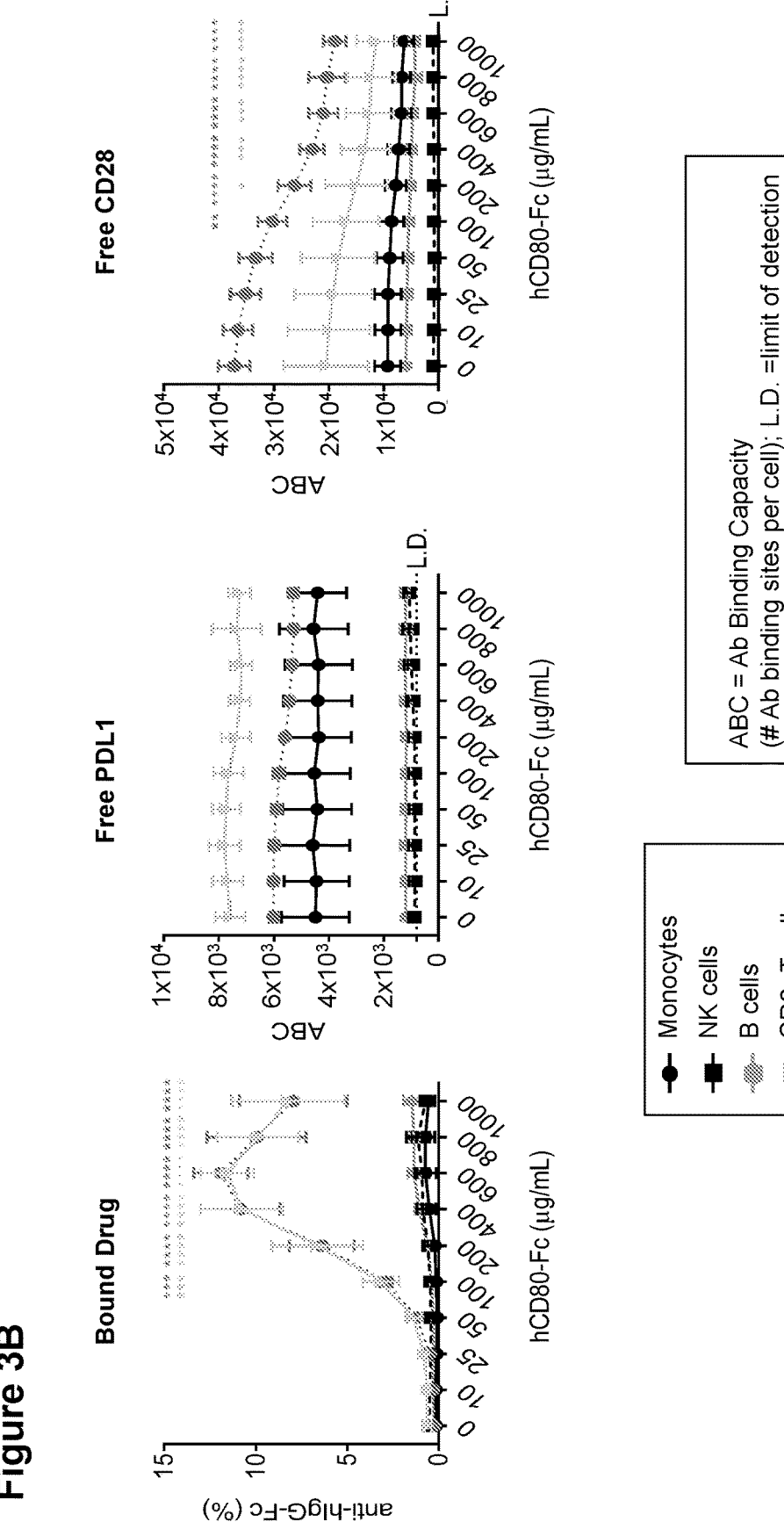

PD-L1 was detected on T cells and monocytes, but CD28 was detected primarily on CD4+ and CD8+ T cells. FIG. 3B shows that hCD80-Fc bound, in a concentration-dependent manner, to both CD4+ and CD8+ T cells, with significant detection of bound drug at concentrations as low as 100 µg/mL. The binding of hCD80-Fc revealed a decrease in free CD28 on CD4+ and CD8+ T cells, but no changes were detected in PD-L1 levels on T cells or monocytes. CTLA-4 was not detected on any immune cell type evaluated. Thus, these results demonstrate that hCD80-Fc primarily binds CD4+ and CD8+ T cells from human PBMCs through CD28 engagement.

Figure 4A:
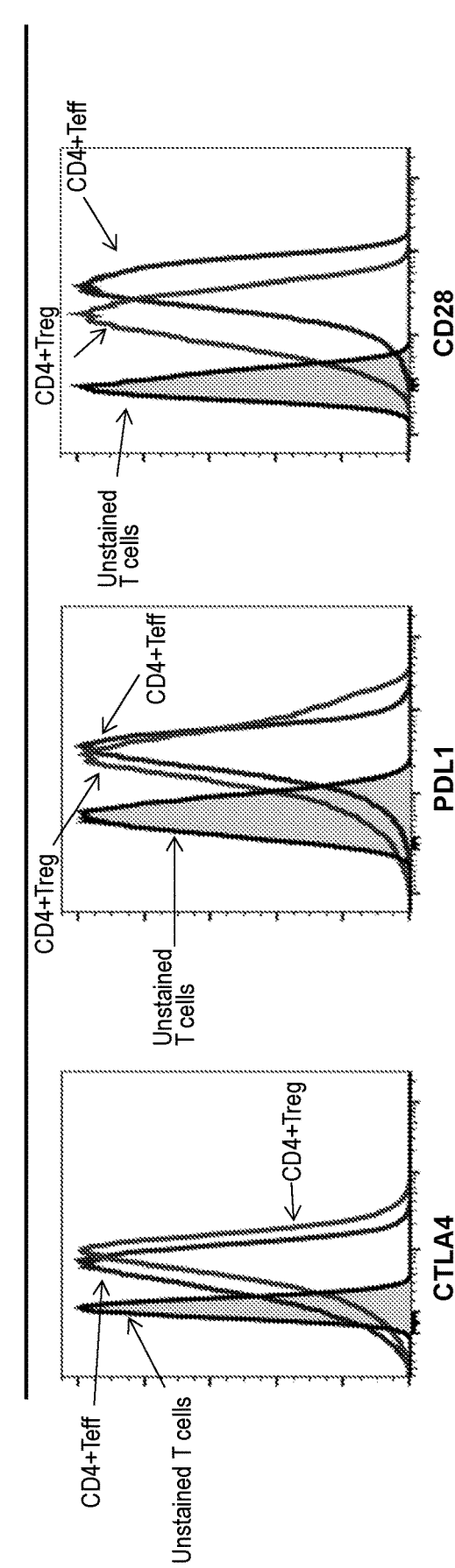
FIGS. 4A and 4B: In vitro-expanded CD4+ Teff and CD4+ Treg were evaluated for hCD80-Fc engagement and receptor occupancy. (A) CD80 ligand expression was evaluated by flow cytometry. Representative histograms are shown comparing ligand expression between unstained T cells, CD4+ Teff and CD4+ Treg. (B) Increasing concentrations of hCD80-Fc were incubated with T cells and hCD80-Fc engagement was measured both via biotin-labeled anti-hIgG-Fc binding followed by streptavidin Alexa488 ("bound drug") and by detection of CD80 ligands with competing Ab clones ("free" CTLA-4, PD-L1 or CD28) enumerated as Antibody Binding Capacity (ABC) values. L.D., limit of detection of ABC. Graphs depict mean±SD of n=2-3 donors. ANOVA-based statistical testing was performed for drug concentrations against no drug (0 µg/mL) where $*p<0.05$, $p<0.01$, $*p<0.001$ was considered significant. (See Example 2.)
Figure 4B:
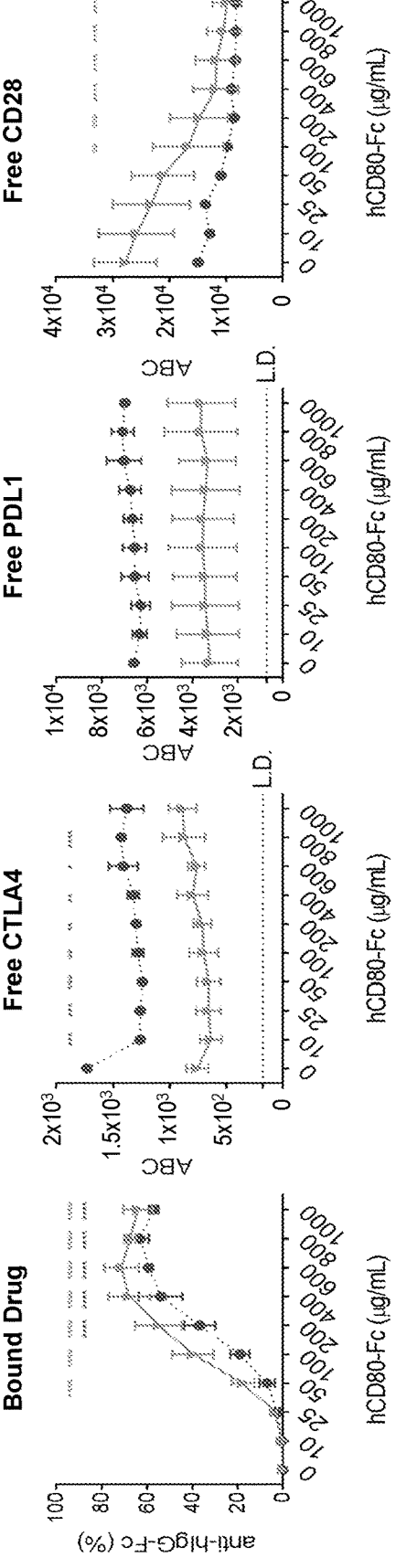

Human in vitro-expanded CD4+ Teff and CD4+ Tregs were evaluated for hCD80-Fc engagement of CTLA-4, PD-L1, and CD28. Human in vitro-expanded CD4+ Teff and CD4+ Tregs have been shown to express CTLA-4, PD-L1, and CD28 (FIG. 4A). hCD80-Fc bound both CD4+ Teff and Tregs in a concentration-dependent manner, with hCD80-Fc binding being detected as low as 50 µg/mL and saturating binding at approximately 400 µg/mL (FIG. 4B). This binding caused a trending decrease in free CTLA-4 in CD4+ Tregs only, while a decrease of free CD28 on CD4+ Teff and Tregs cells was detected (FIG. 4B). Free PD-L1 levels did not change even with exposure to increasing concentrations of hCD80-Fc (FIG. 4B). This data demonstrates that hCD80-Fc engages both CTLA-4 and CD28 on CD4+ Teff and CD4+ Tregs cells Example 3: mCD80-Fc Inhibits Growth of Tumors that do not Express PD-L1 in a CT26 Syngeneic Mouse Model The data from Examples 1 and 2 demonstrate that CD80 does not engage with PD-L1. Thus, to determine if PD-L1 engagement is needed for mCD80-Fc to exert its anti-tumor activity, CT26 PD-L1 knock-out tumor cells were used in an in vivo syngeneic mouse model. Unlike xenograft models, syngeneic mouse models possess a functional immune system and therefore are useful in evaluating cancer immunotherapies, which function by harnessing the endogenous immune response. CT26 is a murine colorectal carcinoma derived from BALB/c mice that expresses high levels of PD-L1. In this study, a genetically-engineered CT26 tumor (CT26 PD-L1 KO) that does not express PD-L1 was used. Immuno-competent BALB/c mice were inoculated with CT26 PD-L1 KO tumor cells. The mice were placed into three groups for treatment with the following: (1) Mouse IgG2a (control); (2) mCD80-Fc; or (3) untreated control. The mice were treated with 0.3 mg/kg mouse IgG2a (group 1) or 0.3 mg/kg mCD80-Fc (group 2) on days 4, 7, and 11 (days post-inoculation) by intravenous injection. See Table 1. The average tumor size when treatment began was 90 $mm^3$. The study concluded on day 21.

TABLE 1

| Group | Treatment | Dosing (mg/kg, schedule, route) | Mice (n) |
|---|---|---|---|
| 1 | Mouse IgG2a | 0.3 mg/kg on D4, D7, D11 200 µL IV | 15 |
| 2 | mCD80-Fc | 0.3 mg/kg on D4, D7, D11 200 µL IV | 15 |
| 3 | n/a | n/a | 15 |

Figure 5:
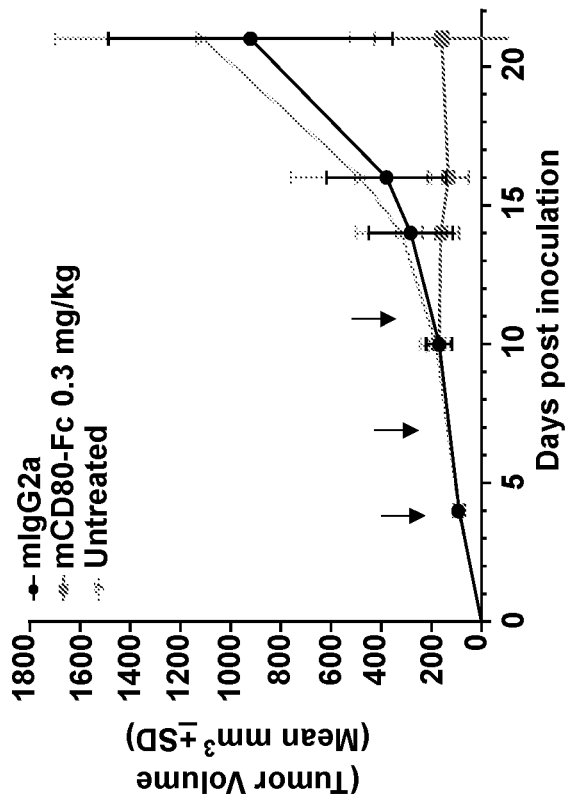
FIG. 5 Average tumor growth in all groups and individual tumor volumes on day 21 are shown. Immuno-competent BALB/c mice were inoculated with CT26 PD-L1 KO tumor cells. Treatment was initiated 4 days post-inoculation, when tumors reached approximately 80 mm³. Mice were treated with mCD80-Fc at 0.3 mg/kg on days 4, 7, and 11. mCD80-Fc significantly inhibited tumor growth (p=0.0004 over mIgG2a control; p<0.0001 over untreated group). (See Example 3)
Figure 5:
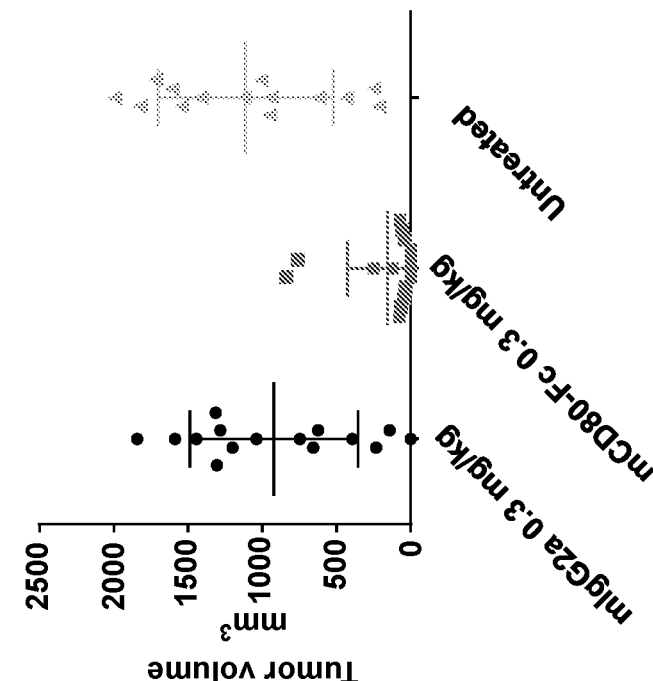

FIG. 5 shows that average tumor volume increased in the mIgG2a and untreated control groups, but the mCD80-Fc group showed significant inhibition of tumor growth (p=0.0004 over mouse IgG2a control; p<0.0001 over untreated group). Also, no adverse effects were detected from treatment with mIgG2a or mCD80-Fc, including changes in body weight (data not shown). These data provide an in vivo demonstration that mCD80-Fc treatment is surprisingly not dependent on PD-L1 expression on tumor cells.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

TABLE OF SEQUENCES
The table below provides a listing of certain
sequences referenced herein.

| SEQ. ID. NO. | Description | Sequence |
|---|---|---|
| 1 | Human CD80 ECD sequence (without signal sequence) | VIHVTKEVKEVATLSCGHNVSVEELAQTRIYWQ KEKKMVLTMMSGDMNIWPEYKNRTIFDITNNLS IVILALRPSDEGTYECVVLKYEKDAFKREHLAEV TLSVKADFPTPSISDFEIPTSNIRRIICSTSGGFPEPH LSWLENGEELNAINTTVSQDPETELYAVSSKLDF NMTTNHSFMCLIKYGHLRVNQTFNWNTTKQEH FPDN |
| 2 | Mouse CD80 ECD sequence (without signal sequence) | VDEQLSKSVKDKVLLPCRYNSPHEDESEDRIYW QKHDKVVLSVIAGKLKVWPEYKNRTLYDNTTY SLIILGLVLSDRGTYSCVVQKKERGTYEVKHLAL VKLSIKADFSTPNITESGNPSADTKRITCFASGGFP KPRFSWLENGRELPGINTTISQDPESELYTISSQLD FNTTRNHTIKCLIKYGDAHVSEDFTWEKPPEDPP DSKN |
| 3 | Fc human IgG1 | EPKSSDKTHTCPPCPAPELLGGPSVFLFPPKPKDT LMISRTPEVTCVVVDVSHEDPEVKFNWYVDGVE VHNAKTKPREEQYNSTYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPGK |
| 4 | Mouse CD80 ECD mouse Fc IgG2a (Fc portion underlined) | VDEQLSKSVKDKVLLPCRYNSPHEDESEDRIYW QKHDKVVLSVIAGKLKVWPEYKNRTLYDNTTY SLIILGLVLSDRGTYSCVVQKKERGTYEVKHLAL VKLSIKADFSTPNITESGNPSADTKRITCFASGGFP KPRFSWLENGRELPGINTTISQDPESELYTISSQLD FNTTRNHTIKCLIKYGDAHVSEDFTWEKPPEDPP DSKNEPRGPTIKPCPPCKCPAPNLLGGPSVFIFPPK IKDVLMISLSPIVTCVVVDVSEDDPDVQISWFVN NVEVHTAQTQTHREDYNSTLRVVSALPIQHQDW MSGKEFKCKVNNKDLPAPIERTISKPKGSVRAPQ VYVLPPPEEEMTKKQVTLTCMVTDFMPEDIYVE WTNNGKTELNYKNTEPVLDSDGSYFMYSKLRV EKKNWVERNSYSCSVVHEGLHNHHTTKSFSRTP GK |
| 5 | Human CD80 ECD Human Fc IgG1 WT (Fc portion underlined) | VIHVTKEVKEVATLSCGHNVSVEELAQTRIYWQ KEKKMVLTMMSGDMNIWPEYKNRTIFDITNNLS IVILALRPSDEGTYECVVLKYEKDAFKREHLAEV TLSVKADFPTPSISDFEIPTSNIRRIICSTSGGFPEPH LSWLENGEELNAINTTVSQDPETELYAVSSKLDF NMTTNHSFMCLIKYGHLRVNQTFNWNTTKQEH FPDNEPKSSDKTHTCPPCPAPELLGGPSVFLFPPK PKDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQPR EPQVYTLPPSRDELTKNQVSLTCLVKGFYPSDIA VEWESNGQPENNYKTTPPVLDSDGSFFLYSKLTV DKSRWQQGNVFSCSVMHEALHNHYTQKSLSLSP GK |
| 6 | human PD-L1 (mature, without signal sequence) | FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |

What is claimed is:

1. A method of treating a PD-L1 negative tumor in a subject, the method comprising:
   (a) selecting a subject having a PD-L1 negative tumor, wherein the PD-L1 negative tumor comprises a tumor proportion score (TPS) of less than 5% as determined by immunohistochemistry (IHC), and
   (b) administering to the subject a composition comprising CD80 extracellular domain (ECD) fusion molecules, wherein the CD80 ECD fusion molecules comprise a human CD80 ECD and a human IgG1 Fc domain.

2. The method of claim 1, wherein the tumor is a solid tumor.

3. The method of claim 1, wherein the subject is afflicted with colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, or endometrial cancer.

4. The method of claim 1, wherein the subject is afflicted with a cancer that is recurrent or progressive after surgery, chemotherapy, radiation therapy, or a combination thereof.

5. The method of claim 1, wherein the CD80 ECD fusion molecules are sialylated.

6. The method of claim 5, wherein the sialylated CD80 ECD fusion molecules comprise 15-60 moles of SA per mole of fusion protein.

7. The method of claim 1, wherein the human CD80 ECD comprises the amino acid sequence of SEQ ID NO:1.

8. The method of claim 1, wherein the human IgG1 Fc domain comprises the amino acid sequence of SEQ ID NO:3.

9. The method of claim 8, wherein the Fc domain of human IgG1 is linked to the carboxy terminus of the ECD of human CD80.

10. The method of claim 1, wherein the CD80 ECD fusion molecules comprise the amino acid sequence of SEQ ID NO:5.

11. The method of claim 1, which comprises administering about 0.07 mg to about 70 of the CD80 ECD fusion molecules to the subject.

12. The method of claim 1, wherein the composition is administered to the subject once every three weeks.

13. The method of claim 1, wherein the composition is administered intravenously.

14. The method of claim 1, wherein the subject has not received prior therapy with a PD-1/PD-L1 antagonist.

15. The method of claim 1, wherein the subject has received prior therapy with at least one anti-angiogenic agent.

16. The method of claim 1, wherein the subject is afflicted with a melanoma that has a BRAF mutation.

17. A method of treating a PD-L1 negative tumor in a human patient, the method comprising:
   (a) selecting a subject having a PD-L1 negative tumor, wherein the PD-L1 negative tumor comprises a tumor proportion score (TPS) of less than 5% as determined by immunohistochemistry (IHC), and
   (b) administering to the patient a composition comprising about 0.07 mg to about 70 mg CD80 extracellular domain (ECD) fusion molecules, wherein each of the CD80 ECD fusion molecules comprises the amino acid sequence of SEQ ID NO:5.

18. The method of claim 17, wherein the composition comprises sialylated CD80 ECD fusion molecules having 15-60 moles of SA per node of fusion protein.

19. The method of claim 1, wherein the TPS score is calculated by the following equation:

$$TPS = \left[\frac{\text{number of } PDL1 \text{ stained tumor cells}}{\text{total number of viable tumor cells}}\right] \times 100.$$

20. The method of claim 17, wherein the TPS score is calculated by the following equation:

$$TPS = \left[\frac{\text{number of } PDL1 \text{ stained tumor cells}}{\text{total number of viable tumor cells}}\right] \times 100.$$

21. The method of claim 1, wherein the tumor comprises a TPS of less than 1%.

22. The method of claim 17, wherein the tumor comprises a TPS of less than 1%.

* * * * *

SEQUENCE LISTING

<160> NUMBER OF SEQ ID NOS: 6

<210> SEQ ID NO 1
<211> LENGTH: 208
<212> TYPE: PRT
<213> ORGANISM: Artificial Sequence
<220> FEATURE:
<223> OTHER INFORMATION: Human CD80 ECD sequence (without signal
      sequence)

<400> SEQUENCE: 1

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 2
<211> LENGTH: 209
<212> TYPE: PRT
<213> ORGANISM: Artificial Sequence
<220> FEATURE:
<223> OTHER INFORMATION: Mouse CD80 ECD sequence (without signal
      sequence)

<400> SEQUENCE: 2

```
Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
    50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
```

-continued

```
                    85                    90                    95
Leu Ala Leu Val Lys Leu Ser Ile Lys Ala Asp Phe Ser Thr Pro Asn
            100                    105                    110

Ile Thr Glu Ser Gly Asn Pro Ser Ala Asp Thr Lys Arg Ile Thr Cys
        115                    120                    125

Phe Ala Ser Gly Gly Phe Pro Lys Pro Arg Phe Ser Trp Leu Glu Asn
    130                    135                    140

Gly Arg Glu Leu Pro Gly Ile Asn Thr Thr Ile Ser Gln Asp Pro Glu
145                    150                    155                    160

Ser Glu Leu Tyr Thr Ile Ser Ser Gln Leu Asp Phe Asn Thr Thr Arg
                165                    170                    175

Asn His Thr Ile Lys Cys Leu Ile Lys Tyr Gly Asp Ala His Val Ser
            180                    185                    190

Glu Asp Phe Thr Trp Glu Lys Pro Pro Glu Asp Pro Pro Asp Ser Lys
        195                    200                    205

Asn
```

```
<210> SEQ ID NO 3
<211> LENGTH: 232
<212> TYPE: PRT
<213> ORGANISM: Artificial Sequence
<220> FEATURE:
<223> OTHER INFORMATION: Fc human IgG1

<400> SEQUENCE: 3

Glu Pro Lys Ser Ser Asp Lys Thr His Thr Cys Pro Pro Cys Pro Ala
1               5                    10                    15

Pro Glu Leu Leu Gly Gly Pro Ser Val Phe Leu Phe Pro Pro Lys Pro
            20                    25                    30

Lys Asp Thr Leu Met Ile Ser Arg Thr Pro Glu Val Thr Cys Val Val
        35                    40                    45

Val Asp Val Ser His Glu Asp Pro Glu Val Lys Phe Asn Trp Tyr Val
    50                    55                    60

Asp Gly Val Glu Val His Asn Ala Lys Thr Lys Pro Arg Glu Glu Gln
65                    70                    75                    80

Tyr Asn Ser Thr Tyr Arg Val Val Ser Val Leu Thr Val Leu His Gln
                85                    90                    95

Asp Trp Leu Asn Gly Lys Glu Tyr Lys Cys Lys Val Ser Asn Lys Ala
            100                    105                    110

Leu Pro Ala Pro Ile Glu Lys Thr Ile Ser Lys Ala Lys Gly Gln Pro
        115                    120                    125

Arg Glu Pro Gln Val Tyr Thr Leu Pro Pro Ser Arg Asp Glu Leu Thr
    130                    135                    140

Lys Asn Gln Val Ser Leu Thr Cys Leu Val Lys Gly Phe Tyr Pro Ser
145                    150                    155                    160

Asp Ile Ala Val Glu Trp Glu Ser Asn Gly Gln Pro Glu Asn Asn Tyr
                165                    170                    175

Lys Thr Thr Pro Pro Val Leu Asp Ser Asp Gly Ser Phe Phe Leu Tyr
            180                    185                    190

Ser Lys Leu Thr Val Asp Lys Ser Arg Trp Gln Gln Gly Asn Val Phe
        195                    200                    205

Ser Cys Ser Val Met His Glu Ala Leu His Asn His Tyr Thr Gln Lys
    210                    215                    220

Ser Leu Ser Leu Ser Pro Gly Lys
225                    230
```

```
<210> SEQ ID NO 4
<211> LENGTH: 442
<212> TYPE: PRT
<213> ORGANISM: Artificial Sequence
<220> FEATURE:
<223> OTHER INFORMATION: Mouse CD80 ECD mouse Fc IgG2a

<400> SEQUENCE: 4

Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
    50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
    130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
            180                 185                 190

Glu Asp Phe Thr Trp Glu Lys Pro Pro Glu Asp Pro Pro Asp Ser Lys
        195                 200                 205

Asn Glu Pro Arg Gly Pro Thr Ile Lys Pro Cys Pro Pro Cys Lys Cys
    210                 215                 220

Pro Ala Pro Asn Leu Leu Gly Gly Pro Ser Val Phe Ile Phe Pro Pro
225                 230                 235                 240

Lys Ile Lys Asp Val Leu Met Ile Ser Leu Ser Pro Ile Val Thr Cys
            245                 250                 255

Val Val Val Asp Val Ser Glu Asp Asp Pro Asp Val Gln Ile Ser Trp
            260                 265                 270

Phe Val Asn Asn Val Glu Val His Thr Ala Gln Thr Gln Thr His Arg
            275                 280                 285

Glu Asp Tyr Asn Ser Thr Leu Arg Val Val Ser Ala Leu Pro Ile Gln
    290                 295                 300

His Gln Asp Trp Met Ser Gly Lys Glu Phe Lys Cys Lys Val Asn Asn
305                 310                 315                 320

Lys Asp Leu Pro Ala Pro Ile Glu Arg Thr Ile Ser Lys Pro Lys Gly
            325                 330                 335

Ser Val Arg Ala Pro Gln Val Tyr Val Leu Pro Pro Pro Glu Glu Glu
            340                 345                 350

Met Thr Lys Lys Gln Val Thr Leu Thr Cys Met Val Thr Asp Phe Met
            355                 360                 365
```

```
Pro Glu Asp Ile Tyr Val Glu Trp Thr Asn Asn Gly Lys Thr Glu Leu
    370             375             380

Asn Tyr Lys Asn Thr Glu Pro Val Leu Asp Ser Asp Gly Ser Tyr Phe
385             390             395             400

Met Tyr Ser Lys Leu Arg Val Glu Lys Lys Asn Trp Val Glu Arg Asn
            405             410             415

Ser Tyr Ser Cys Ser Val Val His Glu Gly Leu His Asn His His Thr
            420             425             430

Thr Lys Ser Phe Ser Arg Thr Pro Gly Lys
            435             440

<210> SEQ ID NO 5
<211> LENGTH: 440
<212> TYPE: PRT
<213> ORGANISM: Artificial Sequence
<220> FEATURE:
<223> OTHER INFORMATION: Human CD80 ECD Human Fc IgG1 WT

<400> SEQUENCE: 5

Val Ile His Val Thr Lys Glu Val Lys Glu Val Ala Thr Leu Ser Cys
1               5               10              15

Gly His Asn Val Ser Val Glu Glu Leu Ala Gln Thr Arg Ile Tyr Trp
            20              25              30

Gln Lys Glu Lys Lys Met Val Leu Thr Met Met Ser Gly Asp Met Asn
        35              40              45

Ile Trp Pro Glu Tyr Lys Asn Arg Thr Ile Phe Asp Ile Thr Asn Asn
    50              55              60

Leu Ser Ile Val Ile Leu Ala Leu Arg Pro Ser Asp Glu Gly Thr Tyr
65              70              75              80

Glu Cys Val Val Leu Lys Tyr Glu Lys Asp Ala Phe Lys Arg Glu His
            85              90              95

Leu Ala Glu Val Thr Leu Ser Val Lys Ala Asp Phe Pro Thr Pro Ser
            100             105             110

Ile Ser Asp Phe Glu Ile Pro Thr Ser Asn Ile Arg Arg Ile Ile Cys
            115             120             125

Ser Thr Ser Gly Gly Phe Pro Glu Pro His Leu Ser Trp Leu Glu Asn
    130             135             140

Gly Glu Glu Leu Asn Ala Ile Asn Thr Thr Val Ser Gln Asp Pro Glu
145             150             155             160

Thr Glu Leu Tyr Ala Val Ser Ser Lys Leu Asp Phe Asn Met Thr Thr
            165             170             175

Asn His Ser Phe Met Cys Leu Ile Lys Tyr Gly His Leu Arg Val Asn
            180             185             190

Gln Thr Phe Asn Trp Asn Thr Thr Lys Gln Glu His Phe Pro Asp Asn
            195             200             205

Glu Pro Lys Ser Ser Asp Lys Thr His Thr Cys Pro Pro Cys Pro Ala
    210             215             220

Pro Glu Leu Leu Gly Gly Pro Ser Val Phe Leu Phe Pro Pro Lys Pro
225             230             235             240

Lys Asp Thr Leu Met Ile Ser Arg Thr Pro Glu Val Thr Cys Val Val
            245             250             255

Val Asp Val Ser His Glu Asp Pro Glu Val Lys Phe Asn Trp Tyr Val
            260             265             270

Asp Gly Val Glu Val His Asn Ala Lys Thr Lys Pro Arg Glu Glu Gln
    275             280             285
```

-continued

```
Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Leu Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
                420                 425                 430

Ser Leu Ser Leu Ser Pro Gly Lys
            435                 440
```

```
<210> SEQ ID NO 6
<211> LENGTH: 272
<212> TYPE: PRT
<213> ORGANISM: Artificial Sequence
<220> FEATURE:
<223> OTHER INFORMATION: Human PD-L1 (mature, without signal sequence)

<400> SEQUENCE: 6
```

```
Phe Thr Val Thr Val Pro Lys Asp Leu Tyr Val Val Glu Tyr Gly Ser
1                   5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
    195                 200                 205
```

-continued

```
Pro Glu Leu Pro Leu Ala His Pro Pro Asn Glu Arg Thr His Leu Val
    210             215             220

Ile Leu Gly Ala Ile Leu Leu Cys Leu Gly Val Ala Leu Thr Phe Ile
225             230             235             240

Phe Arg Leu Arg Lys Gly Arg Met Met Asp Val Lys Lys Cys Gly Ile
            245             250             255

Gln Asp Thr Asn Ser Lys Lys Gln Ser Asp Thr His Leu Glu Glu Thr
            260             265             270
```